US00RE44813E

(19) United States
(12) Reissued Patent
Beale et al.

(10) Patent Number: US RE44,813 E
(45) **Date of Reissued Patent: *Mar. 18, 2014**

(54) ROD REDUCER INSTRUMENTS AND METHODS

(75) Inventors: Jeffrey W. Beale, Bartlett, TN (US); John Stewart Young, Memphis, TN (US)

(73) Assignee: Warsaw Orthopedic, Inc., Warsaw, IN (US)

( * ) Notice: This patent is subject to a terminal disclaimer.

(21) Appl. No.: 12/052,394

(22) Filed: Mar. 20, 2008

Related U.S. Patent Documents

Reissue of:
(64) Patent No.: 6,790,209
Issued: Sep. 14, 2004
Appl. No.: 10/186,780
Filed: Jul. 1, 2002

U.S. Applications:
(63) Continuation of application No. 09/898,626, filed on Jul. 3, 2001, now Pat. No. 6,440,133.

(51) Int. Cl.
*A61B 17/88* (2006.01)

(52) U.S. Cl.
USPC ..... 606/86 A; 606/104; 606/279; 606/99

(58) Field of Classification Search
USPC ..... 606/86 A, 104, 279, 99, 96, 914, 606/205–208, 90, 87, 101
See application file for complete search history.

(56) References Cited

U.S. PATENT DOCUMENTS

| | | | | | |
|---|---|---|---|---|---|
| 3,604,487 | A | * | 9/1971 | Gilbert | 81/443 |
| 3,844,291 | A | * | 10/1974 | Moen | 606/206 |
| 4,411,259 | A | * | 10/1983 | Drummond | 606/86 A |
| 5,020,519 | A | * | 6/1991 | Hayes et al. | 606/237 |
| 5,113,685 | A | * | 5/1992 | Asher et al. | 72/458 |
| 5,209,755 | A | * | 5/1993 | Abrahan et al. | 606/132 |
| 5,308,357 | A | * | 5/1994 | Lichtman | 606/205 |
| 5,314,431 | A | * | 5/1994 | Graziano | 606/101 |
| 5,330,472 | A | * | 7/1994 | Metz-Stavenhagen | 606/53 |
| 5,364,397 | A | * | 11/1994 | Hayes et al. | 606/86 A |
| 5,389,099 | A | * | 2/1995 | Hartmeister et al. | 606/86 A |
| 5,392,978 | A | | 2/1995 | Velez et al. | |
| 5,423,855 | A | | 6/1995 | Marienne | |
| 5,449,361 | A | * | 9/1995 | Preissman | 606/103 |

(Continued)

FOREIGN PATENT DOCUMENTS

| | | | |
|---|---|---|---|
| DE | 42 38 339 | A1 * | 5/1994 |
| DE | 4238339 | | 5/1994 |
| RU | 995769 | | 2/1983 |

OTHER PUBLICATIONS

Sofamor, "Introducteur-Conteur De Tige" (Engineering drawings), Jan. 1, 1994.*

(Continued)

*Primary Examiner* — Pedro Philogene

(57) ABSTRACT

Rod reducers for use in orthopedic surgery are disclosed that include a fastener engaging member and a reducing member coupled together by an actuator assembly. The fastener engaging member can be secured to a fastener engaged to bone or tissue of the patient. The actuator assembly moves the reducing member such that its distal end contacts a rod and moves it toward the fastener.

80 Claims, 15 Drawing Sheets

(56) References Cited

U.S. PATENT DOCUMENTS

| | | | | | |
|---|---|---|---|---|---|
| 5,458,608 | A | * | 10/1995 | Wortrich | 606/139 |
| 5,466,243 | A | * | 11/1995 | Schmieding et al. | 606/232 |
| 5,588,580 | A | | 12/1996 | Paul et al. | |
| 5,616,143 | A | * | 4/1997 | Schlapfer et al. | 606/86 A |
| 5,720,751 | A | * | 2/1998 | Jackson | 606/86 R |
| 5,782,830 | A | * | 7/1998 | Farris | 606/99 |
| 5,782,831 | A | | 7/1998 | Sherman et al. | |
| 5,810,878 | A | | 9/1998 | Burel et al. | |
| 5,855,311 | A | | 1/1999 | Hamblin et al. | |
| 5,899,901 | A | * | 5/1999 | Middleton | 606/914 |
| 5,910,141 | A | * | 6/1999 | Morrison et al. | 606/86 A |
| 5,944,720 | A | * | 8/1999 | Lipton | 606/276 |
| 6,036,692 | A | * | 3/2000 | Burel et al. | 606/86 A |
| 6,042,582 | A | * | 3/2000 | Ray | 606/86 A |
| 6,063,088 | A | * | 5/2000 | Winslow | 606/86 A |
| 6,261,296 | B1 | * | 7/2001 | Aebi et al. | 606/90 |
| 6,440,133 | B1 | * | 8/2002 | Beale et al. | 606/86 A |
| 6,790,209 | B2 | | 9/2004 | Beale et al. | |
| 6,830,570 | B1 | * | 12/2004 | Frey et al. | 623/17.16 |
| 7,156,849 | B2 | | 1/2007 | Dunbar et al. | |
| 7,470,279 | B2 | | 12/2008 | Jackson | |
| 7,611,517 | B2 | | 11/2009 | Lim | |
| 7,625,376 | B2 | | 12/2009 | Brumfield et al. | |
| 2004/0267275 | A1 | | 12/2004 | Cournoyer et al. | |
| 2005/0192570 | A1 | | 9/2005 | Jackson | |
| 2005/0192579 | A1 | | 9/2005 | Jackson | |
| 2005/0228400 | A1 | | 10/2005 | Chao et al. | |
| 2006/0036244 | A1 | | 2/2006 | Spitler et al. | |
| 2006/0074418 | A1 | | 4/2006 | Jackson | |
| 2006/0111712 | A1 | | 5/2006 | Jackson | |
| 2006/0173454 | A1 | | 8/2006 | Spitler et al. | |
| 2007/0270867 | A1 | | 11/2007 | Miller et al. | |
| 2007/0270868 | A1 | | 11/2007 | Dewey | |
| 2007/0276379 | A1 | | 11/2007 | Miller et al. | |
| 2008/0077139 | A1 | | 3/2008 | Landry et al. | |
| 2008/0091213 | A1 | | 4/2008 | Jackson | |
| 2008/0234678 | A1 | | 9/2008 | Gutierrez et al. | |
| 2008/0234765 | A1 | | 9/2008 | Frasier et al. | |

OTHER PUBLICATIONS

Sofamor, "Introducteur-Conteur De Tige" (Engineering frawings), Jan. 1, 1994.*

Sofamor, "Introducteur—Contreur De Tige" (schematic drawings), Jan. 1, 1994.

Laufer and Bowe, CD Horizon Spinal System, Surgical Technique, 1996, Sofamor Danek.

TSRH-3D Vertebral Body Reduction Instrumentation, 2001, Medtronic Sofamor Danek.

Shufflebarger et al., Taking Spinal Instrumentation to a New Dimension, 1995.

Laufer and Bowe, CD Horizon Spinal System, Surgical Technique, 1999, Sofamor Danek.

Moss® Miami 3-Dimensional Instrumentation Product Catalogue, 1995, Depuy Motech, Inc.

Pediatric Isola® Spinal System, Ordering Information for Implants and Instruments, 1998, AcroMed Corporation.

Orthopedic Sourcebook, Instruments for Surgeons, Section K, 1999, Medic.

Z Spinal Instrumentation, Section D, 1987, Zimmer, Inc.

Sofamor Rod Reducer (1994).

* cited by examiner

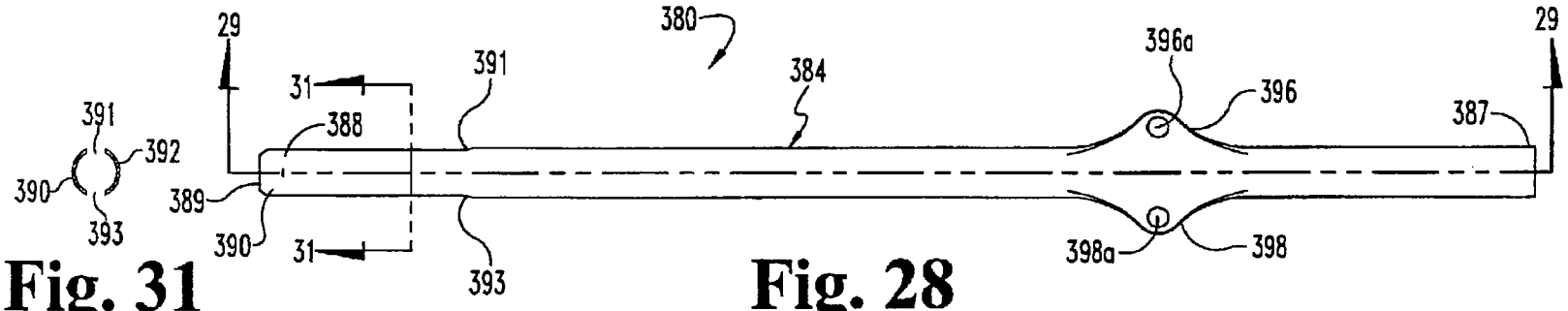
Fig. 28
Fig. 31
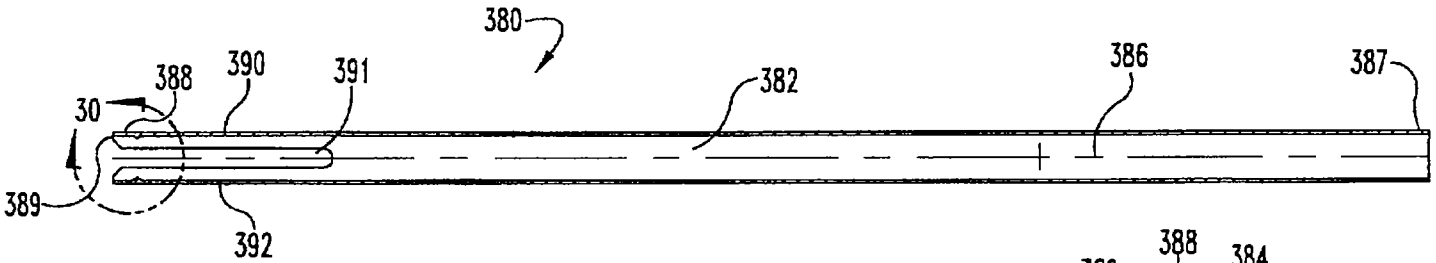
Fig. 29
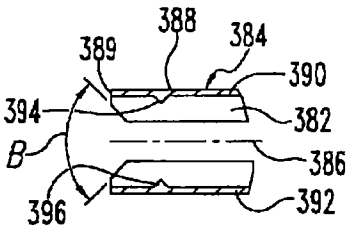
Fig. 30

ROD REDUCER INSTRUMENTS AND METHODS

Matter enclosed in heavy brackets [ ] appears in the original patent but forms no part of this reissue specification; matter printed in italics indicates the additions made by reissue.

CROSS REFERENCE TO RELATED APPLICATION

[The present application] *This application is a reissue of U.S. Pat. No. 6,790,209, issued on Sep. 14, 2004, which is hereby incorporated by reference, as if fully set forth herein. U.S. Pat. No. 6,790,209 matured from U.S. application Ser. No. 10/186,780, filed Jul. 1, 2002. U.S. patent application Ser. No. 10/186,780* is a continuation of U.S. patent application Ser. No. 09/898,626, filed on Jul. 3, 2001 and now issued as U.S. Pat. No. 6,440,133 *filed Aug. 27, 2002*.

FIELD OF THE INVENTION

The present invention concerns surgical instrumentation for moving one part of a surgical implant into adjacent position or contact with another. In particular, the invention contemplates rod reducer instruments for use in placing or moving an orthopedic rod toward a bone fixation element.

BACKGROUND OF THE INVENTION

In the field of orthopedic surgery, and particularly spinal surgery, it is well known to correct an injury, malformation, or other defect by use of an implanted rod affixed to the body part to be corrected. For example, rod systems have been developed for correcting the positioning of and stabilizing the spine, and for facilitating fusion at various levels of the spine. In one such system, the rod is disposed longitudinally along a length of the spine. The rod is preferably bent, either prior to or during surgery, to correspond to the normal curvature of the spine in the particular region being instrumented, or to such other curvature as the surgeon may deem appropriate to correct the defect. For example, the rod can be bent to form a normal kyphotic curvature for the thoracic region of the spine, or to form a normal lordotic curvature for the lumbar region. The rod is engaged to a number of fixation elements fixed to or engaged with the vertebrae along the segment of the spinal column.

A variety of fixation elements can be provided that are configured to engage the vertebrae. For instance, one such fixation element is a laminar hook, configured to engage a lamina of the vertebra. Another prevalent fixation element is a spinal screw which can be threaded into a pedicle or other portion of vertebral bone. Examples of such spinal screws are seen in U.S. Pat. No. 5,005,562 to Cotrel, the disclosure of which is incorporated herein by reference. An alternative type of fixation element is a multi-axial bone screw, such as that as disclosed in U.S. Pat. Nos. 5,797,911 and 5,879,350 to Sherman et al., each of which is also incorporated herein by reference in its entirety. Further types of bone screws, hooks, bolts, or other fixation elements are known in the art.

In one typical spinal procedure, an elongated implant (e.g. a rod) is coupled to two or more fixation elements (e.g. bone screws) that are fixed to opposite sides of the spine or spinous processes. The bone screws are first threaded into a portion of several vertebral bodies, such as the pedicles of these vertebrae. The rod is coupled to the bone screws to provide corrective and stabilizing forces to the spine. Affixing a rod to a bone screw generally requires the rod to be in close adjacent position or in contact with the screw. For example, with respect to bone screws as disclosed in the Cotrel '562 patent and the Sherman '911 and '350 patents identified above, a rod and an implanted screw must be moved with respect to each other so that the rod occupies space within a channel or other opening in the screw. The rod is then coupled to the implanted bone screw using a set screw, plug or other appropriate fastener. The process of placing a rod within or adjacent to an implanted fixation element so that they can be coupled together is termed "reducing" the rod.

Rod reduction is commonly performed by a surgeon using his or her hands and/or rigid tools as pliers, levers or other instrumentation adaptable to create the necessary pushing and/or pulling forces on the implanted screw and rod. Such procedures generally require the surgeon to place the rod directly over the implanted fixation element, intersecting a longitudinal axis of the fixation element. Consequently, access to the rod and the implanted fixation element along that axis, i.e. directly above the opening in the fixation element into which the rod is to be placed, is necessary or at least highly desirable. However, such access can be difficult depending on such factors as the malformation to be corrected and the overall physiology of the patient, and can be very difficult in procedures in which surgical invasiveness is to be minimized, as a result of the small ports or incisions of such procedures. Additionally, with use of mono-axial screws, the physiology of the patient can require that the screw be placed at an angle such that the surgeon would have difficulty accessing and exerting force in the necessary orientation on the rod and/or fixation element. With multi-axial fixation devices, the orientation of an unsecured rod-receiving part of the fixation element can be even more varied with respect to the rod and/or the surgeon. Consequently, the surgeon is still frequently faced with the task of reducing a rod from an awkward angle.

Various attempts in the prior art have been made in providing rod reducing instruments, such as described in U.S. Pat. No. 6,036,692 to Burel et al.; U.S. Pat. No. 5,910,141 to Morrison et al.; and U.S. Pat. No. 5,720,751 to Jackson; each of which is incorporated herein by reference in its entirety. However, needs remain in the industry for rod reducing instruments that can be used efficiently, safely and securely in rod reduction procedures and for rod reduction instruments that can be used in both minimally invasive and open surgical approaches to the site of rod attachment.

SUMMARY OF THE INVENTION

The present invention provides instrumentation for rod reduction during orthopedic surgery that are efficient and convenient to use. The instruments eliminate the need for direct application of manual force to a rod to position it in a desired location relative to a fastener. The instruments can also facilitate attachment of the rod to the fastener, and have application in both open surgical procedures and minimally invasive surgical procedures.

Aspects, objects, advantages, features, embodiments, and benefits of the present invention will be evident upon consideration of the following written description and the accompanying figures, which illustrate embodiments of the invention.

BRIEF DESCRIPTION OF THE DRAWINGS

FIG. 28 is an elevational view of a fastener engaging member comprising a portion of the rod reducer instrument of FIG. 25.

FIG. 29 is a cross-sectional view through line 29-29 of FIG. 28.

FIG. 30 is an enlarged view of the distal end of the fastener engaging member of FIG. 28.

FIG. 31 is a cross-sectional view through line 31-31 of FIG. 28.

DESCRIPTION OF THE ILLUSTRATED EMBODIMENTS

Figure 1:
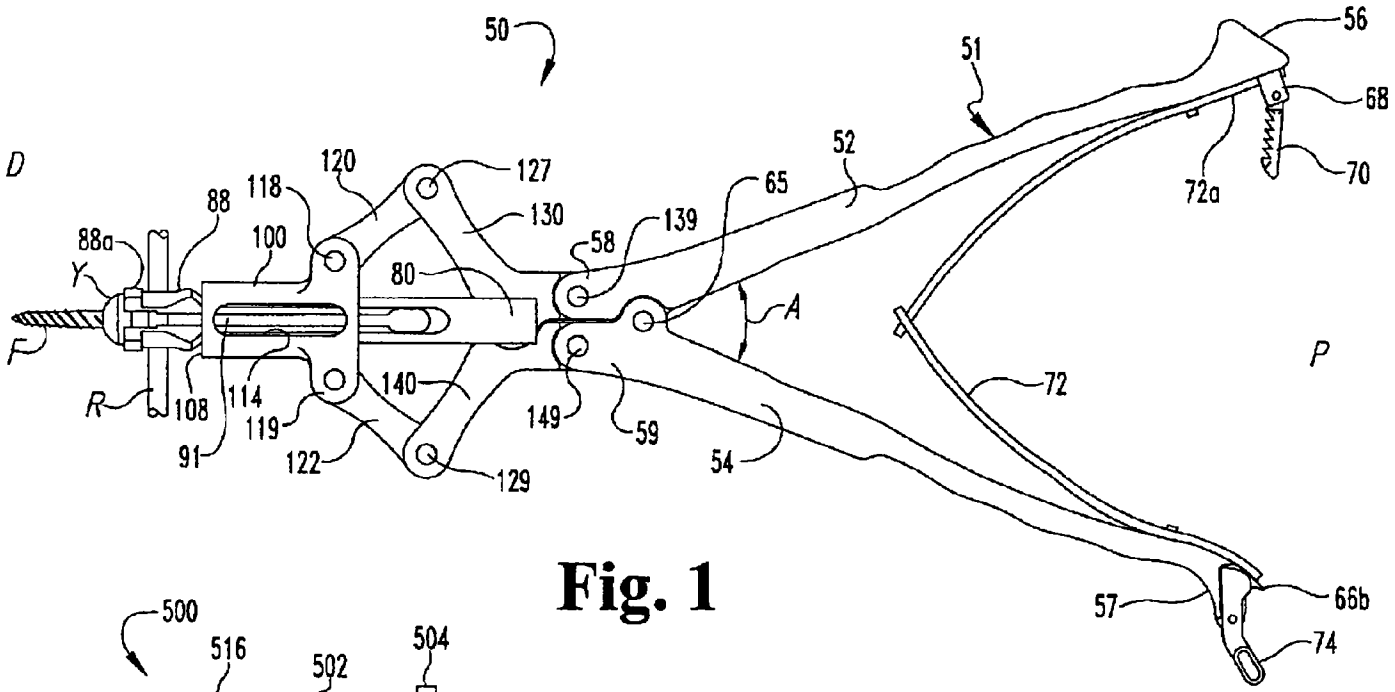
FIG. 1 is a front elevational view of a rod reducer instrument in accordance with one embodiment of the present invention shown in a retracted position.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated therein, are contemplated as would normally occur to one skilled in the art to which the invention relates.

Figure 2:
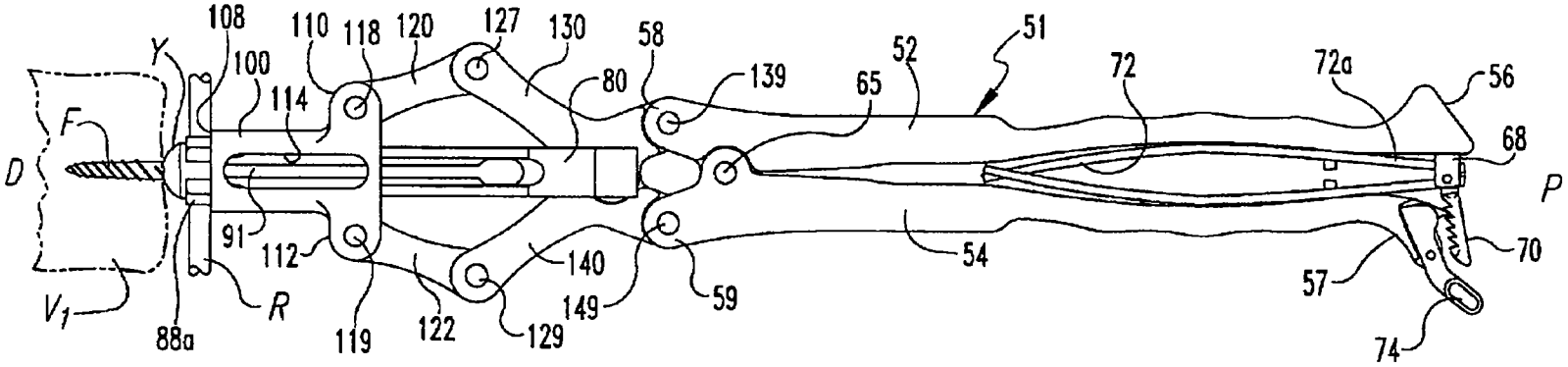
FIG. 2 is a front elevational view of the rod reducer instrument of FIG. 1 shown in a reducing position.
Figure 3:
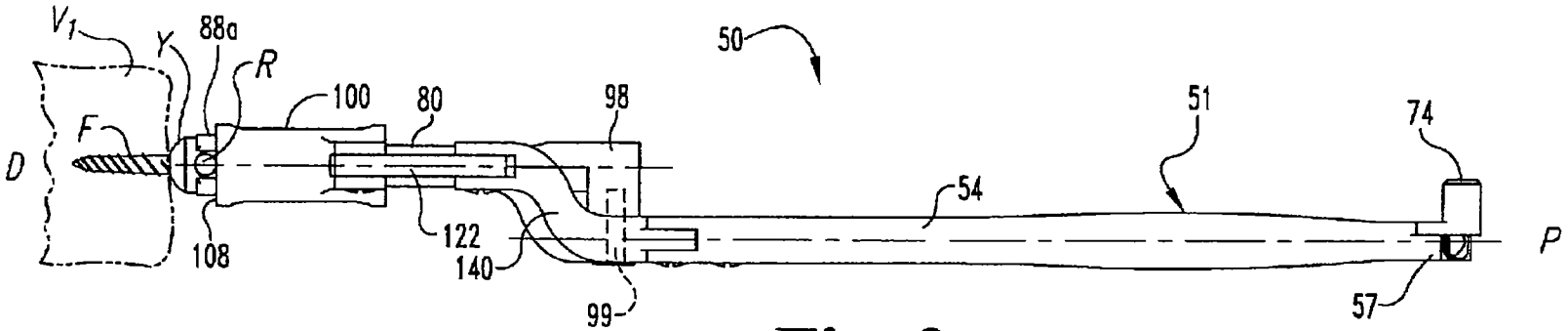
FIG. 3 is a side elevational view of the rod reducer instrument of FIG. 2.

Referring to FIGS. 1-3, there is shown a first embodiment of a rod reducer instrument 50 according to the present invention. In normal use in the patient's body rod reducer instrument 50 is oriented so that its actuator assembly 51 is located proximally, indicated by the letter "P" and accessible by the surgeon, and the opposite end of instrument 50 is oriented distally, indicated by the letter "D", away from the surgeon and towards the operative site. In FIGS. 1-3, the operative site is a vertebral body V1 of the spinal column in which a fastener F is engaged. Fastener F has a yoke Y that allows a rod R to be positioned therein and then secured to fastener F with a set screw or the like. In order to facilitate the surgeon's positioning of rod R in fastener F, rod reducer instrument 50 is engageable to fastener F and positionable against rod R and thereafter operable to move rod R in closer proximity to fastener F such that rod R can be secured to fastener F. Fastener F can be a multi-axial or uni-axial screw, a hook, or other bone or tissue engaging device. Rod R can be any elongated implant element of any size or shape so long as it can be secured to fastener F.

Rod reducer instrument 50 includes a fastener engaging member 80 and a reducing member 100 coupled together by an actuator assembly 51 such that reducing member 100 is movable proximally and distally with respect to fastener engaging member 80. Fastener engaging member 80 is engageable to fastener F and reducing member 100 is movable to contact rod R and push it toward fastener F. In the illustrated embodiment, reducing member 100 is slidably disposed about fastener engaging member 80, and rod R is captured in fastening engaging member 80 when reducing member 100 is in a retracted position as shown in FIG. 1. Reducing member 100 is movable distally with respect to fastener engaging member 80 by actuator assembly 51 to contact rod R and position rod R into yoke Y of fastener F as shown in FIGS. 2 and 3. Fastener engaging member 80 has a passage 82 (FIG. 7) extending therethrough through which a set screw or cap and a driver (not shown) can be extended to engage the set screw to yoke Y and securing rod R therein.

With further reference to FIGS. 6-9 in conjunction with FIGS. 1-3, fastener engaging member 80 will now be further described. In the illustrated embodiment, fastener engaging member 80 includes a body 84 having a longitudinal axis 86 and an enlarged distal portion 88. Although body 84 is shown as having a generally cylindrical cross-section perpendicular to axis 86, it is understood that body 84 can have a cross-section of any appropriate shape, such as oval, square, or regularly or irregularly polygonal. Body 84 is hollow in a preferred embodiment, having passage 82 extending between and opening at proximal end 87 and distal end 89 of body 84.

Body 84 also includes first and second flex arms 90 and 92. In the illustrated embodiment, flex arms 90 and 92 have slots 91 and 93 extending therebetween. Slot 91 includes a relieved portion 91a and slot 93 includes a relieved portion 93a to facilitate flexion of flex arms 90 and 92 away from one another as distal portion 88 is positioned over yoke Y of fastener F. In the illustrated embodiment, distal portion 88 includes prongs 94 and 96 through which slots 91 and 93 extend. Each prong 94, 96 includes a rod channel 94a, 96a in communication with slots 91, 93 and configured to receive rod R therein. Flex arms 90 and 92 can be apart in their natural state, so that they can be squeezed together by reducing member 100 contacting the enlarged distal portion 88 to hold a fastener F therein, and released to move apart from each other and release fastener F. Alternatively, flex arms 90, 92 can be together in their natural state, so that they can be forced apart by insertion of a fixation element or other application of force, and will naturally clamp on or around fastener F.

Figure 9:
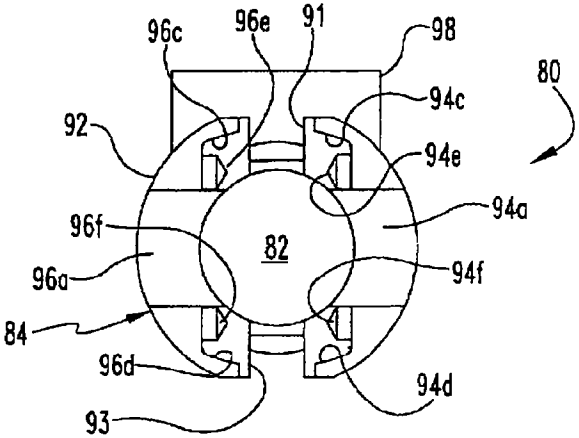
FIG. 9 is a distal end elevational view of the fastener engaging member of FIG. 6.
Figure 6:
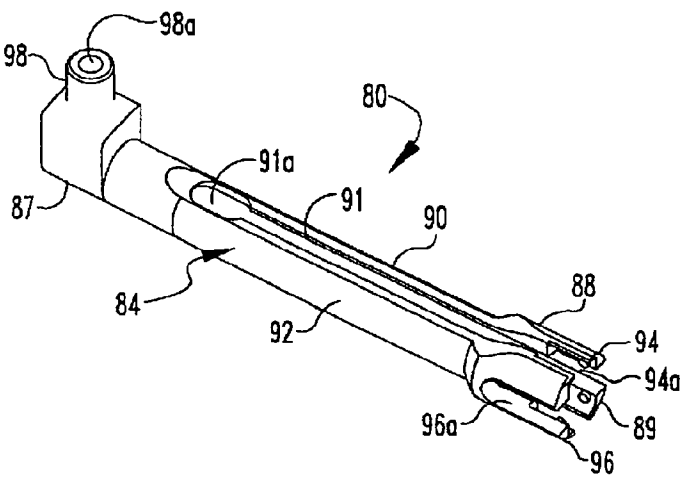
FIG. 6 is a perspective view of a fastener engaging member comprising a portion of the rod reducer instrument of FIGS. 1 and 4.
Figure 7:
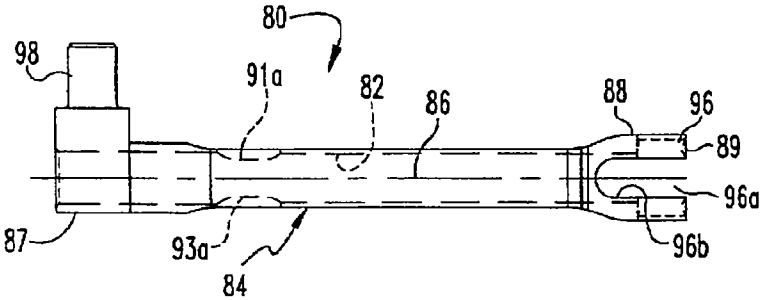
FIG. 7 is a side elevational view of the fastener engaging member of FIG. 6.

Prongs 94 and 96 are substantially identically configured, and therefore they will both be described by reference to prong 96 as shown in FIGS. 7 and 9. Prong 96 includes a wall 96b that surrounds a portion of rod channel 96a. Prong 94 also has interior surfaces 96c and 96d extending between respective ones of the slots 91 and 93 and rod channel 96a. Interior surfaces 96c and 96d are sized and shaped to match the profile of the portion of yoke Y of fastener F that is positionable thereagainst. Extending from interior surfaces 96c and 96d are protrusions 96e and 96f, respectively. Protrusions 96e and 96f have a size, shape and depth that allows insertion into an indentation or hole formed in yoke Y of fastener F. For example, the multi-axial bone screw disclosed in U.S. Pat. No. 5,797,911 includes four opposed round indentations in its exterior portion. Protrusions 96e and 96f, along with the identical protrusions on prong 94, are designed to fit into these indentations. However, it should be understood that prongs 94 and 96 can be configured to fit other sizes, shapes or depths of indentations, or otherwise to connect to other bone fixation elements.

It will be understood that fastener engaging member 80 need not include flex arms 90, 92, but rather be a formed from a substantially solid body having an appropriately-shaped socket distal end for engaging fastener F and including a rod channel which receives rod R. Such a solid body could also include spring-loaded protrusions that allow passage of the distal end over yoke Y until the protrusions engage in the corresponding indentations. Furthermore, such a distal end could include only a pair of protrusions on the inner wall oriented toward rod channels 94a, 94b and engage indentations or holes formed on corresponding locations of yoke Y of fastener F, such as shown in the aforementioned '911 patent. Other means for connecting fastener engaging member 80 to fastener F are also contemplated, including a snap rings, set screws, or an interference fit, to name a few.

Proximal end 87 of fastener engaging member 80 further includes a lateral extension 98 having a hole 98a formed therein. As shown in FIG. 3, this hole 98a of lateral extension 98 receives a pin or fastener 99 to couple fastener engaging member 80 to actuator assembly 51. Fastener engaging member 80 is coupled to actuator assembly 51 such that fastener engaging member 80 remains stationary while components of actuator assembly 51 pivot about fastener 99.

Figure 10:
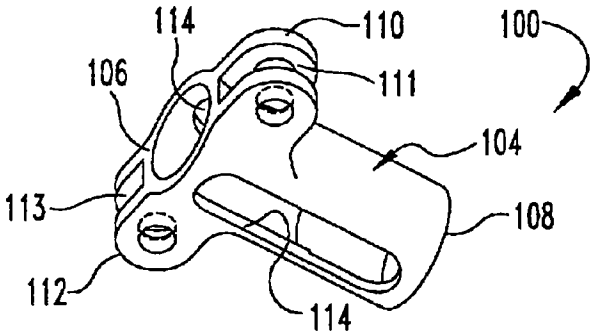
FIG. 10 is a perspective view of a reducing member comprising a portion of the rod reducer instrument of FIGS. 1 and 4.
Figure 11:
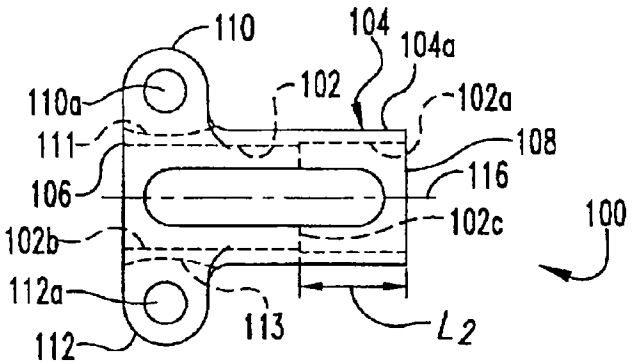
FIG. 11 is a side elevational view of the reducing member of FIG. 10.

Rod reducer instrument 50 further includes reducing member 100 positioned about fastener engaging member 80. Referring now to FIGS. 10-11 in conjunction with FIGS. 1-3, reducing member 100 includes a substantially cylindrical body 104 extending between a proximal end 106 and a distal end 108. Reducing member 100 also includes an internal passage 102 extending along longitudinal axis 116 between and opening at proximal end 106 and distal end 108. Passage 102 of reducing member 100 is dimensioned to be slidable with respect to fastener engaging member 80. Reducing member 100 further includes a first ear 110 and a diametrically opposite ear 112. Ears 110 and 112 are pivotally coupled to actuator assembly 51.

Passage 102 can include distal portion 102a defined by an extension portion 104a of body 104. Passage 102 also includes a proximal portion 102b in communication with distal portion 102a and opening at proximal end 106. Distal portion 102a is larger in diameter than proximal portion 102b and is sized to receive enlarged distal portion 88 of fastener engaging member 80 therein. A lip 102c is defined between distal portion 102a and proximal portion 102b and contacts enlarged rim 88a to limit the distance of distal movement of reducing member 100 with respect to fastener engaging member 80. The length L2 of passage 102a and extension 104a of reducing member 100 can vary from 0 millimeters up to 20 millimeters or more, thus allowing the surgeon to select a rod reducer instrument 50 having an extension 104a/distal passage 102a of appropriate length for the distance of rod reduction beyond distal end 89 that is desired. It is further contemplated that proximal portion 102b can include a further inwardly stepped portion or other means for contacting or reducing the spacing between fastener engaging member 80 and reducing member 100 to limit the amount of wobble or play of reducing member 100 with respect to fastener engaging member 80.

In procedures using multiple fasteners F along the spine, yokes Y can have extended lengths from the head of fastener F that allows rod R to be spaced at various distances from each fastener F. The ability to select from rod reducer instruments having different extension lengths L2 enables the spacing between each fastener F and rod R in yoke Y to be controlled and varied, such as would be desirable in a spondylolisthesis reduction technique. After the desired rod position in the extended yoke Y is obtained, a set screw is placed through passage 82 and into yoke Y to maintain rod R at this desired position.

Figure 1A:
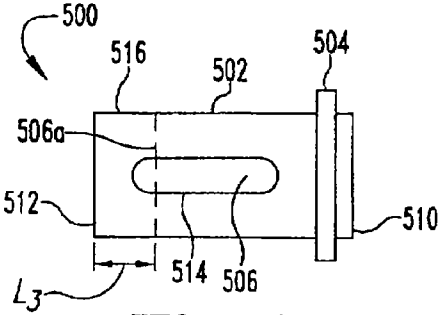
FIG. 1a is an elevational view of an extension member useable with the rod reducer instruments of the present invention.

In another form, rod reducer instrument 50 has a passage 102 with a distal portion 102a that is sized to engage enlarged distal portion 88 of fastener engaging member 80. Distal end 88 contacts enlarged rim 88a to limit the amount of distal displacement of reducing member 100. Proximal portion 102b fits closely around fastener engaging member 80 to limit or eliminate wobble or play of reducing member 100 with respect to fastener engaging member 80. In order to adapt this form of rod reducer instrument 50 for spondylolisthesis procedures, an extension member 500 is provided as shown in FIG. 1a. Extension member 500 has a body 502 with a rim 504 about a proximal end thereof to facilitate placement and removal over reducing member 100. Extension member 500 has a passage 506 extending between and opening at the proximal end 510 and the distal end 512 of extension member 500. Passage 506 is configured so that extension member 500 can be positioned about reducing member 100 with its proximal end adjacent ears 118, 119 and held with respect thereto via frictional engagement, threaded engagement, a set screw or the like. Extension member 500 has a distal portion 516 about distal passage portion 506a that has length L3 which extends beyond distal end 108 of reducing member 100 to allow reduction of rod R distally beyond distal end 108. Length L3 can provided in any increment of 1 millimeter or more. It is further contemplated that rod reducer instrument 50 can be provided in a kit with a number of extension members 500 having different lengths L3 to allow the surgeon to select the amount of rod reduction desired beyond distal end 108 of reducing member 100. In use, rod reducer instrument 50 is used without extension 500 for initial reduction of rod R into the elongated yoke Y and the rod is provisionally secured in this initial position with a set screw. An extension member 500 of desired length is then placed over reducing member 100 and rod R is further reduced to a desired position and the set screw advanced into the yoke to secure rod R in its desired position.

Actuator assembly 51 includes a first arm 52 and a second arm 54, and is operable to selectively move reducing member 100 proximally and distally along fastener engaging member 80 with longitudinal axes 86 and 116 substantially aligned. Contact between the distal ends 58, 59 of arms 52, 54 of actuator assembly 51 prevent reducing member 100 from being retracted too far proximally. As reducing member 100 is moved distally, its distal end 108 contacts rod R and moves it distally towards fastener F. The surgeon can then insert the set screw or cap through passage 82 of fastener engaging member 80 to secure rod R in yoke Y. Passage 82 can be sized and configured to closely fit with the driver used to install the set screw to ensure proper alignment between the set screw and the yoke. Reducing member 100 can be provided with slots 114, 115 that are alignable with slots 91, 93 of fastener engaging member 80. This allows the surgeon to visualize passage 82 and the internal portion of yoke Y during rod reduction and set screw placement to verify proper alignment and positioning. Extension member 500 could also be provided with slots 514 through its body 504 to allow such visualization when it is used.

Figure 12:
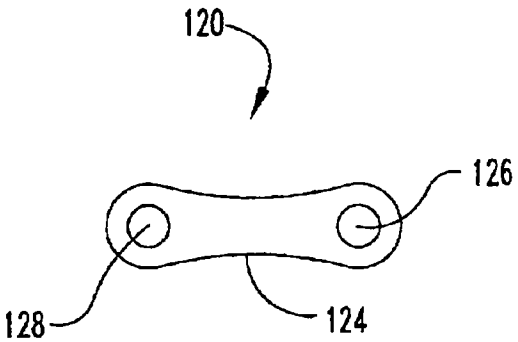
FIG. 12 is an elevational view of a link comprising a portion of the rod reducer instrument of FIGS. 1 and 4.

First ear 110 can be provided with a female receptacle 111 into which one end of a first link 120 of actuator assembly 51 can be placed. Similarly, second ear 112 can be provided with a female receptacle 113 into which one end of a second link 122 of actuator assembly 51 can be placed. First and second links are identical, and will be described further with reference to first link 120 shown in FIG. 12. Link 120 includes a body 124 having first hole 126 at one end thereof and a second hole 128 at an opposite end thereof. First hole 126 is alignable with first ear holes 110a of first ear 110, and the first hole of second link 122 is similarly alignable with second ear holes 112a of second ear 112. Links 122, 124 are pivotally secured to ears 110, 112, respectively, via pins 118, 119 respectively.

Figure 14:
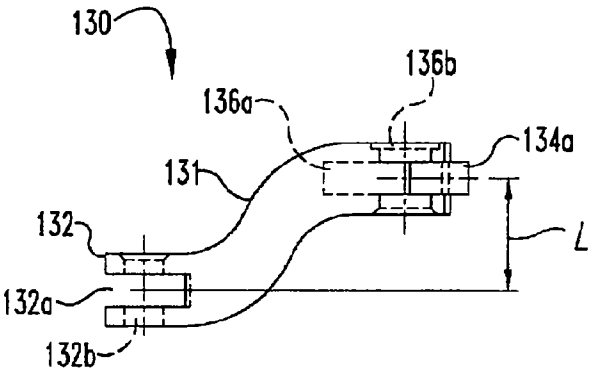
FIG. 14 is an elevational view of the first offset pivot arm of FIG. 13.
Figure 15:
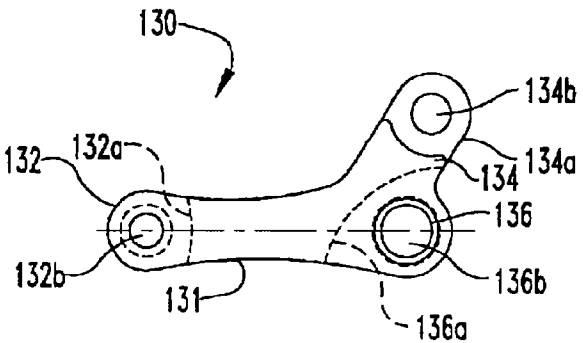
FIG. 15 is an elevational view of the first offset pivot arm of FIG. 13 rotated ninety degrees from its FIG. 13 orientation.
Figure 13:
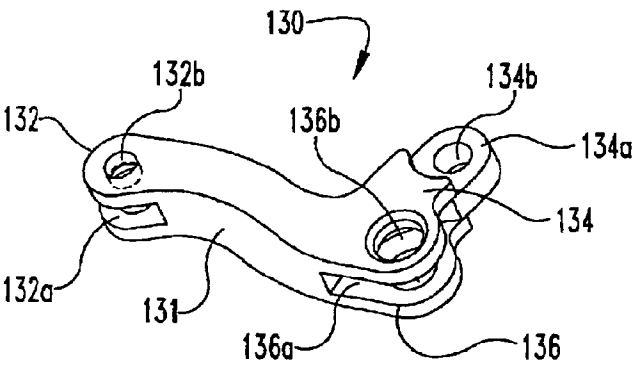
FIG. 13 is a perspective view of a first offset pivot arm comprising a portion of the rod reducer instrument of FIGS. 1 and 4.

Second hole 128 of link 120 is pivotally connected to a first offset pivot arm 130 of actuator assembly 51 by pin 127, and the identical second hole of second link 122 is pivotally coupled to second offset pivot arm 140 of actuator assembly 51 by pin 129. Referring now to FIGS. 13-15 along with FIGS. 1-3, first offset pivot arm 130 includes a body 131 defining a lateral offset L to position the proximal portion of actuator assembly 51 away from passage 82 of fastener engaging member 80. Body 131 has a distal end 132 defining a female receptacle 132a and holes 132b extending therethrough in communication with female receptacle 132a. First link 120 is positionable in female receptacle 132a with its second hole aligned with holes 132b. Body 131 extends from distal end 132 to proximal end 134 and forms a lateral offset L therebetween, as discussed further below with respect to second offset pivot arm 140. Proximal end 134 includes a proximal male connector 134a having a hole 134b formed therethrough. Proximal male connector 134a is stepped down to a reduced thickness from body portion 131 to facilitate pivotal engagement with a female receptacle 58a at distal end 58 of first arm 52 of actuator assembly 51.

Figure 17:
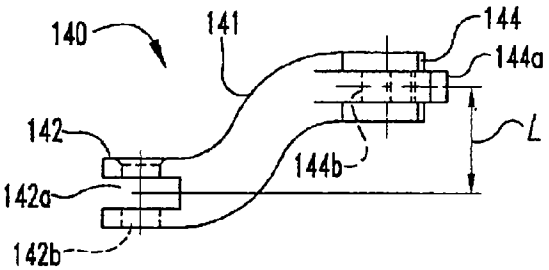
FIG. 17 is an elevational view of the second offset pivot arm of FIG. 16.
Figure 18:
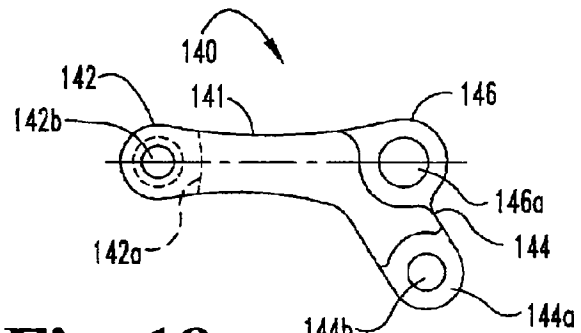
FIG. 18 is an elevational view of the second offset pivot arm of FIG. 16 rotated ninety degrees from its FIG. 16 orientation.
Figure 16:
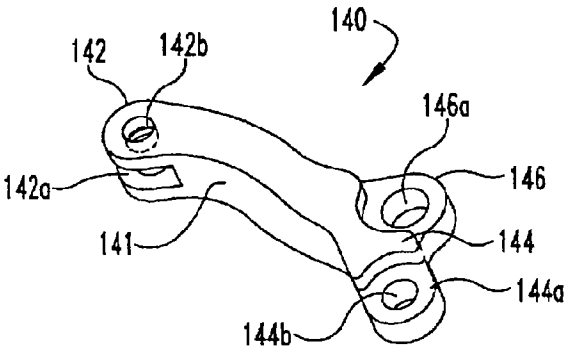
FIG. 16 is a perspective view of a second offset pivot arm comprising a portion of the rod reducer instrument of FIGS. 1 and 4.

Referring now to FIGS. 16-18 along with FIGS. 1-3, second offset pivot arm 140 includes a body 141 defining a lateral offset L to position the proximal portion of actuator assembly 51 away from passage 82 of fastener engaging member 80. Body 141 has a distal end 142 defining a female receptacle 142a and holes 142b extending therethrough in communication with female receptacle 142a. Second link 122 is positionable in female receptacle 142a with its second hole aligned with holes 142b. Body 141 extends from distal end 142 to proximal end 144 and forms a lateral offset L therebetween that is the same as the offset L for first offset pivot arm 130. In one specific embodiment, lateral offset L is about 17 millimeters; however, it should be understood that other lateral offset distances are also contemplated, ranging from no lateral offset up to 30 millimeters or more. Proximal end 144 includes a proximal male connector 144a having a hole 144b formed therethrough. Proximal male connector 144a is stepped down to a reduced thickness from body portion 141 to facilitate pivotal engagement with a female receptacle 59a at distal end 59 of second arm 54 of actuator assembly 51.

As shown in FIGS. 16-18, second offset pivot arm 140 includes a medial male connector 146 adjacent proximal end 144 that is stepped down to a reduced thickness from body 141. Medial male connector 146 includes a hole 146a extending therethrough. Referring to FIGS. 13-15, first offset pivot arm 130 includes a medial female connector 136 adjacent proximal end 134 that defines a female receptacle 136a sized to receive medial male connector 146 of second offset pivot arm 140. Medial female connector 136 includes holes 136b extending therethrough in communication with female receptacle 136a. Fastener 99 is extendable through holes 136b and hole 146a to pivotally couple first offset pivot arm 130 to second offset pivot arm 140. As discussed above, fastener 99 is also attached to hole 98a of lateral extension 98 to secure fastener engaging member 80 to actuator assembly 51 while allowing first offset pivot arm 130 and second offset pivot arm 140 to pivot with respect thereto.

Figure 19:
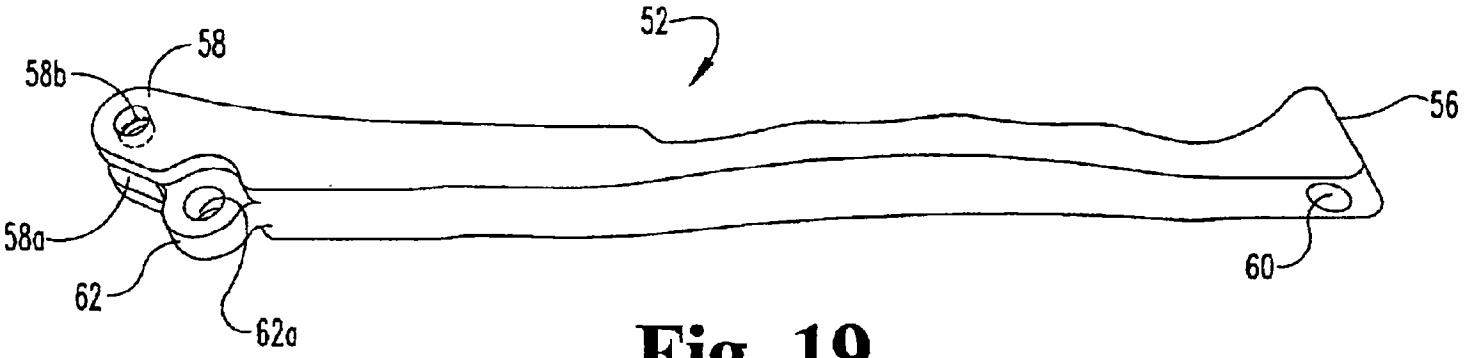
FIG. 19 is a perspective view of a first arm comprising a portion of the rod reducer instrument of FIG. 1.
Figure 20:
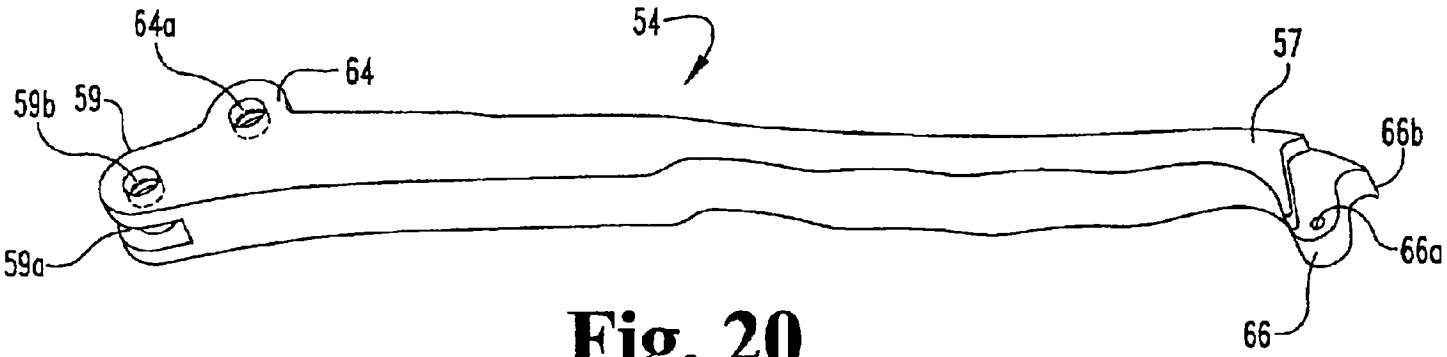
FIG. 20 is a perspective view of a second arm comprising a portion of the rod reducer instrument of FIG. 1.
Figure 22:
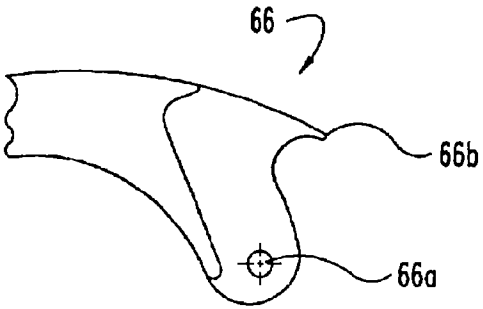
FIG. 22 is an enlarged elevation view of the proximal end of the second arm rotated ninety degrees from its orientation in FIG. 21.

Referring now to FIGS. 19 and 20, first arm 52 and second arm 54 of actuator assembly 51 will be described. First arm 52 extends between proximal end 56 and distal end 58 and can include an arcuate profile therealong to accommodate the hands and fingers of a surgeon's grip. Distal end 58 includes female receptacle 58a having holes 58b in communication therewith. Female receptacle 58a is sized to receive proximal male connector 134a of first offset pivot arm 130 therein. Pin 139 extends through holes 58b and hole 134b of first offset pivot arm 130 to pivotally couple first arm 52 thereto. Second arm 54 extends between proximal end 57 and distal end 59 and can include an arcuate profile therealong to accommodate the hands and fingers of a surgeon's grip. Distal end 59 includes female receptacle 59a having holes 59b in communication therewith. Female receptacle 59a is sized to receive proximal male connector 144a of second offset pivot arm 140 therein. Pin 149 extends through holes 59b and hole 144b of second offset pivot arm 140 to pivotally couple second arm 54 thereto.

First arm 52 has a medially extending male connector 62 defining a hole 62a therethrough. Second arm 54 has a medially extending female connector 64 defining a receptacle (not shown) in communication with holes 64a. The receptacle of female connector 64 is sized to receive male connector 62, and a pin 65 extends through holes 64a and 62a to pivotally couple first arm 52 and second arm 54 to one another.

Rod reducer instrument 50 includes a locking mechanism that holds actuator assembly 51 in a closed position such as shown in FIG. 2. While a specific locking mechanism will be described, it should be understood that the present invention contemplates other means of holding actuator assembly 51 in a closed position.

Figure 24:
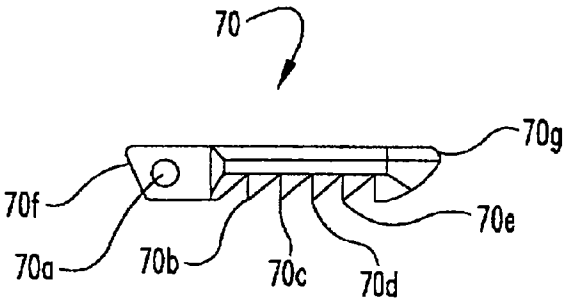
FIG. 24 is a side elevational view of a ratchet arm comprising a portion of the rod reducer instrument of FIGS. 1 and 4.
Figure 21:
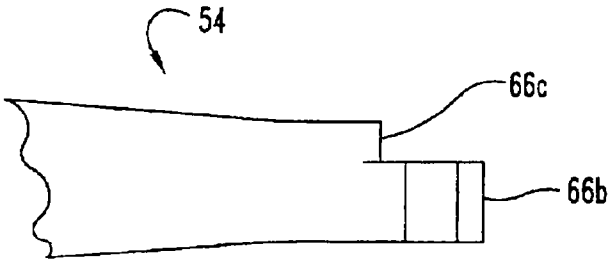
FIG. 21 is an elevational view of the proximal end of the second arm of FIG. 20.
Figure 23:
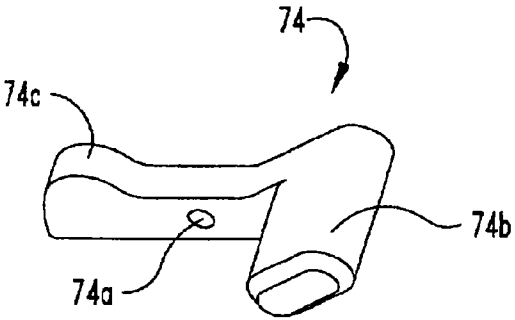
FIG. 23 is a perspective view of a releaser comprising a portion of the rod reducer instrument of FIGS. 1 and 4.

Proximal end 57 of second arm 54 further includes a tip 66 that is stepped down to a reduced thickness from that of second arm 54. Tip 66 includes a hole 66a formed therein and a finger 66b extending proximally therefrom and pointing laterally away from first arm 52. Proximal end 56 of first arm 52 has a hole 60 formed in a medial side thereof into which ratchet bracket 68 (FIG. 1) can be secured via a press fit, threaded connection, welded connection or the like. Ratchet 70 is pivotally coupled to ratchet bracket 68 and extends medially from first arm 52 toward second arm 54. As shown in further detail in FIG. 24, ratchet 70 includes a hole 70a through which a pin can be placed to pivotally couple ratchet 70 to ratchet bracket 68. Ratchet 70 further includes a number of teeth 70b, 70c, 70d, 70e each of which can interlock with finger 66b to hold actuator assembly 51 in a closed position.

Rod reducer instrument 50 further includes a leaf spring 72 extending between and engaged to the medial sides of first arm 52 and second arm 54 to provide a biasing force that normally biases actuator assembly 51 to an open position. Leaf spring 72 includes a first end 72a extending through ratchet bracket 68 and away from first arm 52 to contact an inclined end wall 70f of ratchet 70 to normally bias medial end 70g of ratchet 70 in the distal direction. When actuator assembly 51 is closed, first arm 52 is adjacent second arm 54 as shown in FIG. 2, and one of the teeth of ratchet 70 engages finger 66b of second arm 54. First end 72a of spring 72 biases ratchet 70 toward finger 66b to maintain this engagement.

To facilitate disengagement of ratchet 70 and finger 66b, a thumb release lever 74 is provided that is pivotally coupled to tip 66. Lever 74 has a hole 74a through which a pin may be placed to pivotally couple lever 74 to hole 66a of tip 66. Lever 74 includes a press member 74b and an opposite nub 74c. When arms 52, 54 are in their closed position as shown in FIG. 2, press member 74 can be pushed distally, thereby raising nub 74c into contact with ratchet 70 and lifting ratchet 70 off of finger 66b to allow arms 52, 54 to return to their normally biased open position of FIG. 1. Wall 66c of tip 66 blocks distal pivoting movement of nub 74c.

A method for using rod reducer instrument 50 will now be described. The surgeon has positioned fastener F into vertebra V1 and placed rod R in the proximity of yoke Y of fastener F. Rod reducer instrument 50 is in its normally biased open position of FIG. 1 in which arms 52, 54 form angle A. In one specific embodiment, angle A is 45 degrees; however other values for angle A are also contemplated. Rod reducer instrument 50 is introduced through an open incision or an access port to fastener F. Fastener engaging member 80 is placed around rod R so that rod R is in rod channels 94a, 96a. Distal portion 88 is placed over yoke Y, and flex arms 90, 92 allow prongs 94, 96 to move outwardly to pass over yoke Y until protrusions 94e, 94f, 96e, 96f engage indentations in yoke Y. It is further contemplated that flex arms 90, 92 can be bent away from one another and predisposed to an open position such that distal portion 88 is loosely positioned over yoke Y and reducing member 100 moves distally along flex arms 90, 92 and distal portion 88 and pushes flex arms 90, 92 together to allow protrusions 94e, 94f, 96e, 96f to engage indentations in yoke Y.

With rod R in rod channels 94a, 96a and distal portion 88 secured to yoke Y, arms 52, 54 are moved towards one another against the bias of spring 72 until ratchet 70 engages finger 66b. As arms 52, 54 of actuator assembly 51 are moved toward one another, reducing member 100 moves distally along fastener engaging member 80 to push or reduce rod R into yoke Y a sufficient distance to allow attachment of a set screw or cap to yoke Y.

The distal movement of reducing member 100 is effected by distal ends 58, 59 of arms 52, 54, respectively, moving away from one another, which thereby pivots lateral offset pivot arms 130, 140 about fastener 99 so that proximal ends 134, 144 move away from one another and distal ends 132, 142 move towards one and distally, thereby pushing first and second links 120, 122 distally and effecting distal movement of reducing member 100 through the pivotal connection between ears 110, 112 and links 120, 122. Reducing member 100 also engages the enlarged distal portion 88 of fastener engaging member 80 thereby increasing the grip of prongs 94, 96 on yoke Y. The locked actuator assembly 51 holds rod R in its reduced position as the surgeon installs the set screw in yoke Y through passage 82 of fastener engaging member 80. The lateral offset provided by pivot arms 130, 140 facilitate surgeon access since arms 52, 54 are positioned away from the proximal end opening of fastener engaging member 80. Once the set screw is firmly seated in yoke Y, and preferably seated against rod R, lever 74 is pressed to release ratchet 70 from finger 66b so arms 52, 54 and reducing member 100 return to their open position of FIG. 1. Flex arms 90 and 92 allow prongs 94, 96 to be flexed open and release protrusions 94e, 94f, 96e, 96f from yoke Y. Rod reducer instrument 50 can then be removed and the procedure repeated as needed to reduce rod R into other fasteners.

Figure 4:
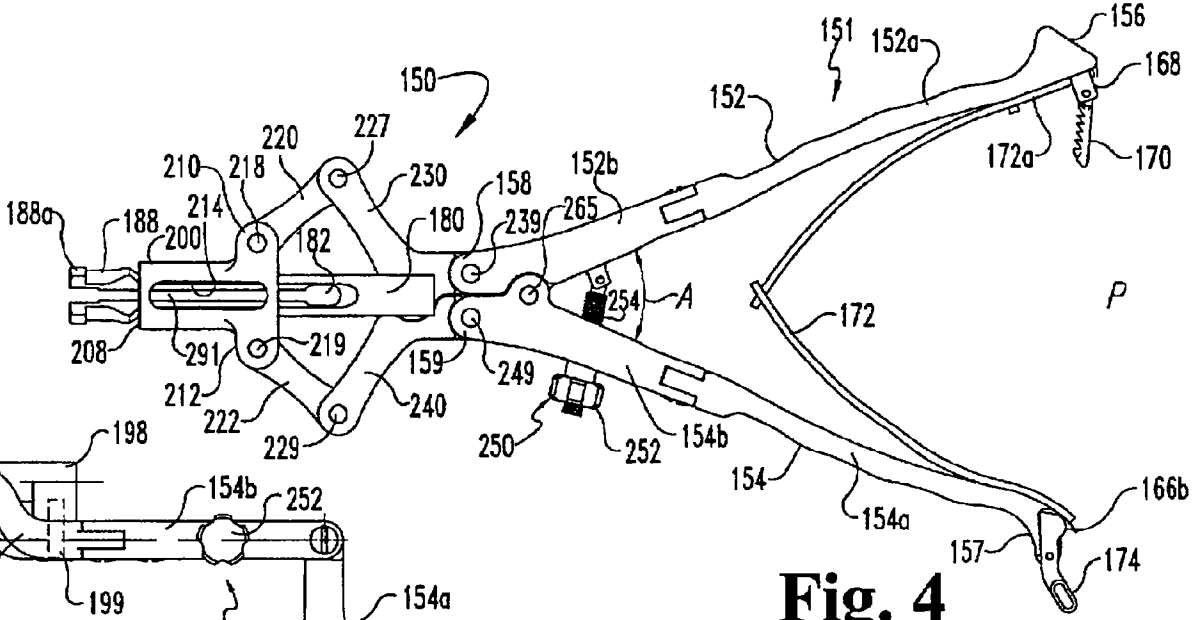
FIG. 4 is a front elevational view of a rod reducer instrument in accordance with an alternate embodiment of the present invention shown in a retracted position.
Figure 5:
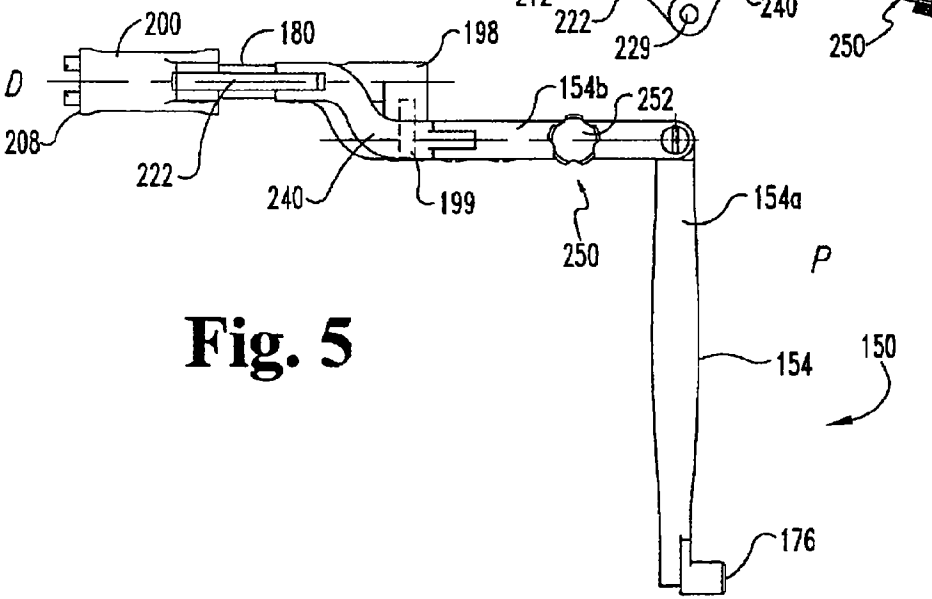
FIG. 5 is a side elevational view of the rod reducer instrument of FIG. 4 with a portion of its actuator assembly pivoted transversely.
Figure 8:
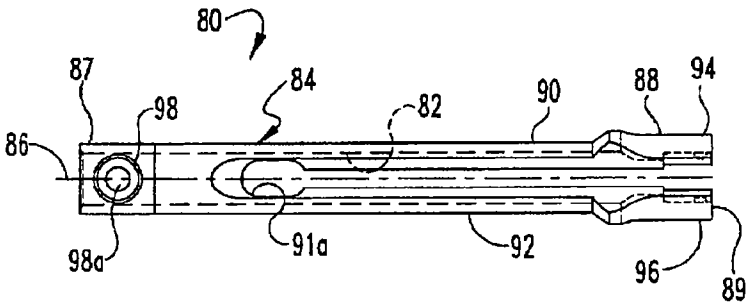
FIG. 8 is a side elevational view of the fastener engaging member of FIG. 6 rotated ninety degrees about its longitudinal axis from its FIG. 7 orientation.

Referring now to FIGS. 4 and 5, an alternate embodiment rod reducer instrument 150 is provided. Except as otherwise discussed herein, rod reducer instrument 150 is identical to rod reducer instrument 50, and elements of rod reducer instrument 150 that are the same as the elements of rod reducer instrument 50 are similarly designated but have "100" added to the reference numeral used for that element in the description of rod reducer 50. Rod reducer instrument 150 includes a first arm 152 having a proximal portion 152a pivotally coupled to a distal portion 152b. Rod reducer instrument 150 further has a second arm 154 having a proximal portion 154a pivotally coupled to a distal portion 154b. As shown in FIG. 5, this pivotal connection allows proximal portions 152a, 154a to be pivoted in the same direction transversely to distal portions 152b, 154b and away from passage 182 of fastener engaging member 180, providing the surgeon additional room to access passage 182. Further, the pivoted arm portions 152a, 154a can be used as the surgeon as a means to provide a counter-torque as the set screw is tightened onto rod R.

Rod reducer instrument 150 further includes an adjustment mechanism 250 that allows fine control over movement of first arm 152 and second arm 154 relative to one another. Adjustment mechanism 250 include a thumb nut 252 coupled to a threaded shaft 254. Threaded shaft 254 is pivotally coupled to the medial side of first arm 152 and extends through a hole provided through second arm 154. Thumb nut 252 is positioned on the lateral side of second arm 154. In order to move first arm 152 and second arm 154 towards one another, thumb nut 252 can be threadingly advanced along threaded shaft 254 towards first arm 152. In order to move first arm 152 and second arm 154 away from one another, thumb nut 252 can be threadingly retracted along threaded shaft 254 away from first arm 152.

Figure 25:
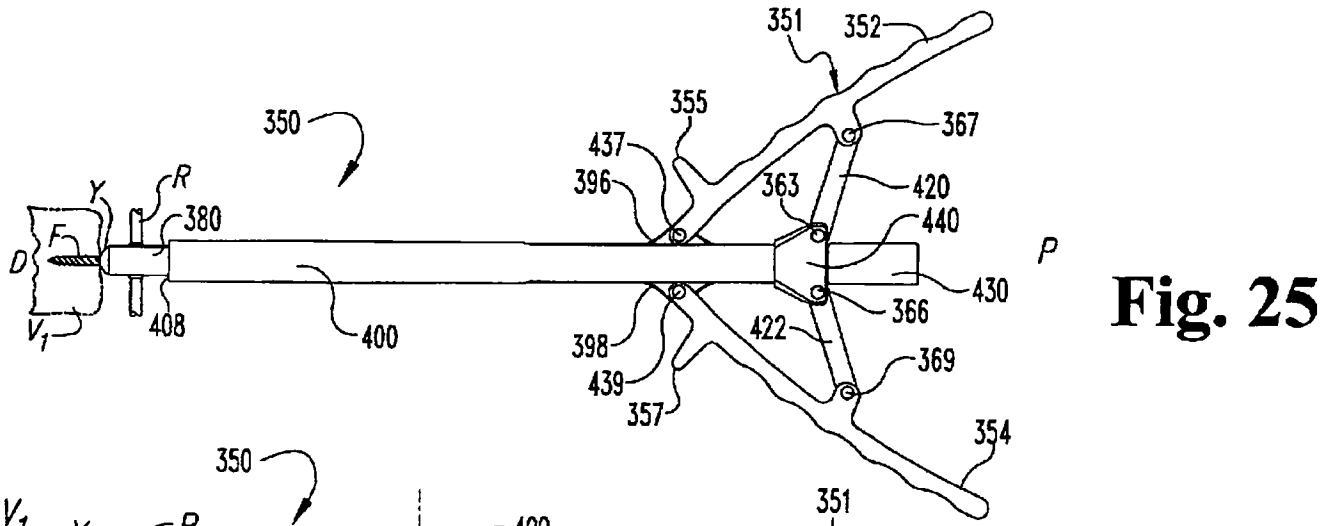
FIG. 25 is a front elevational view of a rod reducer instrument in accordance with a further embodiment of the present invention shown in a retracted position.
Figure 26:
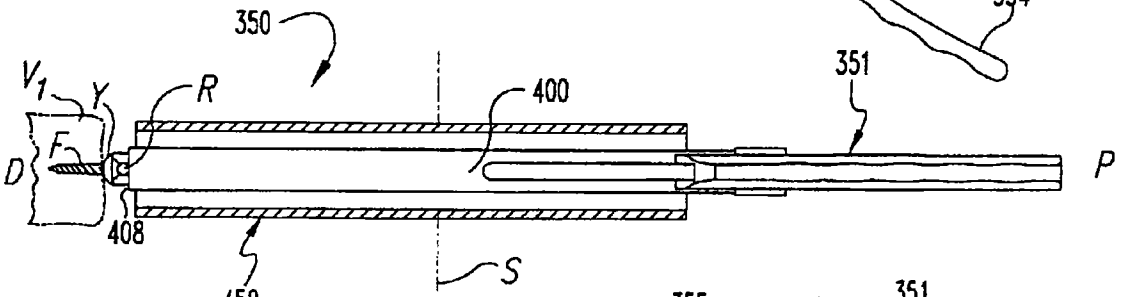
FIG. 26 is a side elevational view of the rod reducer instrument of FIG. 25 shown in a reducing position and extending through an access port.
Figure 27:
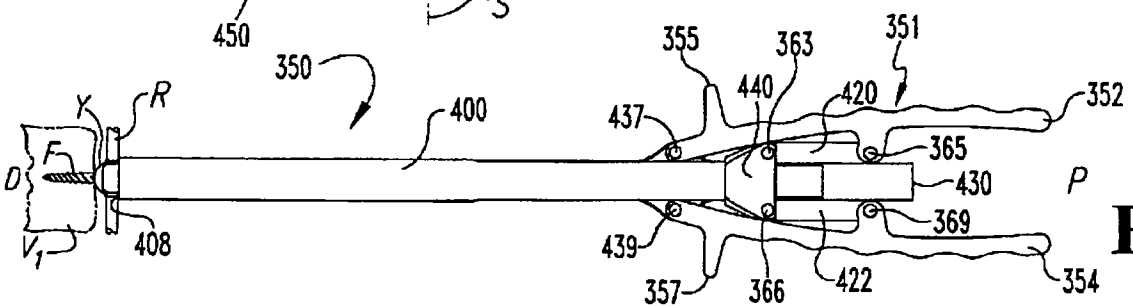
FIG. 27 is the rod reducer instrument of FIG. 25 shown in a reducing position.

Referring to FIGS. 25-27, there is shown a further embodiment of a rod reducer instrument 350 according to the present invention. In normal use in the patient's body rod reducer instrument 350 is oriented so that its actuator assembly 351 is oriented proximally, indicated by the letter "P" and accessible by the surgeon, and the opposite end of instrument 350 is oriented distally, indicated by the letter "D", away from the surgeon and towards the operative site.

Rod reducer instrument 350 includes a fastener engaging member 380 and a reducing member 400 coupled together by an actuator assembly 351 such that reducing member 400 is movable proximally and distally with respect to fastener engaging member 380. Fastener engaging member 380 is engageable to fastener F and reducing member 400 is movable to contact rod R and push it toward fastener F. In the illustrated embodiment, reducing member 400 is slidably disposed about fastener engaging member 380, and rod R is captured in fastening engaging member 380 when reducing member 400 is in a retracted position as shown in FIG. 25. Reducing member 400 is movable distally with respect to fastener engaging member 380 by actuator assembly 351 to contact rod R and position rod R into yoke Y of fastener F as shown in FIGS. 26 and 27. Fastener engaging member 380 has a passage 382 (FIG. 29) extending therethrough through which a set screw or cap and a driver (not shown) can be extended to engage the set screw to yoke Y and securing rod R therein.

With further reference to FIGS. 28-31 in conjunction with FIGS. 25-27, fastener engaging member 380 will now be further described. In the illustrated embodiment, fastener engaging member 380 includes a body 384 having a longitudinal axis 386 and a distal portion 388. Although body 384 is shown as having a generally cylindrical cross-section perpendicular to axis 386, it is understood that body 384 can have a cross-section of any appropriate shape, such as oval, square, or regularly or irregularly polygonal. Body 384 is hollow in a preferred embodiment, having passage 382 extending between and opening at proximal end 387 and distal end 389 of body 384.

Body 384 also includes first and second flex arms 390 and 392. In the illustrated embodiment, flex arms 390 and 392 have slots 391 and 393 extending therebetween. Slots 391 and 393 facilitate flexion of flex arms 390 and 392 away from one another as distal portion 388 is positioned over yoke Y of fastener F. In one embodiment, the distal end opening is tapered at angle B (FIG. 30) to facilitate passage over yoke Y of fastener F. In one specific embodiment, angle B is ninety degrees, however other taper angles are also contemplated. Each slot 391, 393 forms a channel sized to receive rod R therein. Flex arms 390 and 392 can be apart in their natural state, so that they can be squeezed together by reducing member 400 to hold fastener F therein, and released to move apart from each other and release fastener F. Alternatively, flex arms 390, 392 can be together in their natural state, so that they can be forced apart by insertion of a fixation element or other application of force, and will naturally clamp on or around fastener F.

Flex arms 390 and 392 can each further include an inner profile sized and shaped to match the profile of the portion of yoke Y of fastener F that is positionable therein. Extending inwardly from flex arms 390 and 392 are protrusions 394 and 396, respectively. Protrusions 394 and 396 have a size, shape and depth that allows insertion into an indentation or hole formed in yoke Y of fastener F. For example, the multi-axial bone screw disclosed in U.S. Pat. No. 5,797,911 includes two diametrically opposed indentations in its exterior portion. However, it should be understood that flex arms 390 and 392 can be configured to fit other sizes, shapes or depths of indentation, or otherwise to connect to other bone fixation elements.

It will be understood that fastener engaging member 380 need not include flex arms 390, 392, but rather be formed from a substantially solid body having an appropriately-shaped socket distal end for engaging fastener F and including a rod channel to receive rod R. Such a solid body could also include spring-loaded protrusions that allow passage of the distal end over yoke Y until the protrusions engage in the corresponding indentations. Furthermore, such a distal end could include four protrusions as described above with respect to rod reducer instrument 50. Other means for connecting fastener engaging member 380 to fastener F are also contemplated, including snap rings, set screws, or an interference fit, to name a few.

Fastener engaging member 380 further includes a first ear 396 extending laterally therefrom having a hole 396a formed therethrough and a second ear 398 extending laterally therefrom having a hole 398a formed therethrough. As shown in FIG. 25, these ears 396, 398 extend through reducing member 400 for pivotal engagement to actuator assembly 351.

Figure 32:
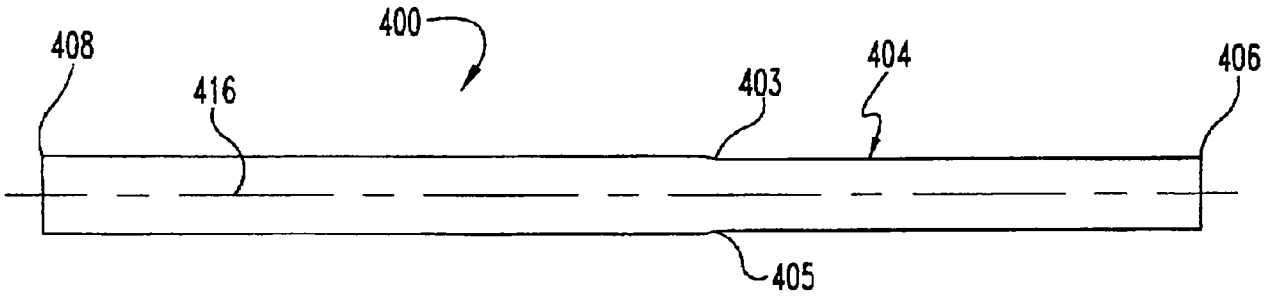
FIG. 32 is an elevational view of a reducing member comprising a portion of the rod reducer instrument of FIG. 25.
Figure 33:
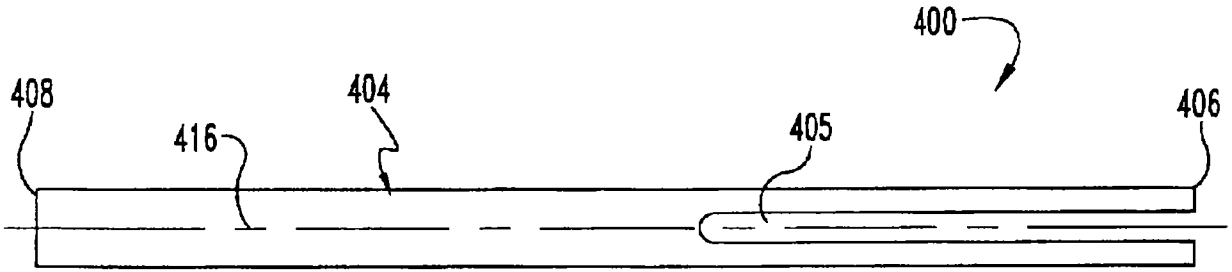
FIG. 33 is an elevational view of the reducing member of FIG. 32 rotated ninety degrees about its longitudinal axis from its orientation in FIG. 32.
Figure 34:
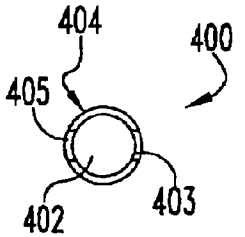
FIG. 34 is an elevational view looking at the proximal end of the reducing member of FIG. 32.

Referring now to FIGS. 32-34 in conjunction with FIGS. 25-27, reducing member 400 includes a substantially cylindrical body 404 extending between a proximal end 406 and a distal end 408. Reducing member 400 also includes an internal passage 402 extending along longitudinal axis 416 between and opening at proximal end 406 and distal end 408. Passage 402 is sized so that reducing member 400 can be positioned about fastener engaging member 380. Reducing member 400 further includes a first slot 403 to receive first ear 396 therethrough and a diametrically opposite second slot 405 to receive second ear 398 therethrough. Each of the slots 403, 405 opens at the proximal end of reducing member 400. Reducing member 400 is slidable proximally and distally via actuator assembly 351 along fastener engaging member 380 with longitudinal axes 386 and 416 substantially aligned.

Figure 42:
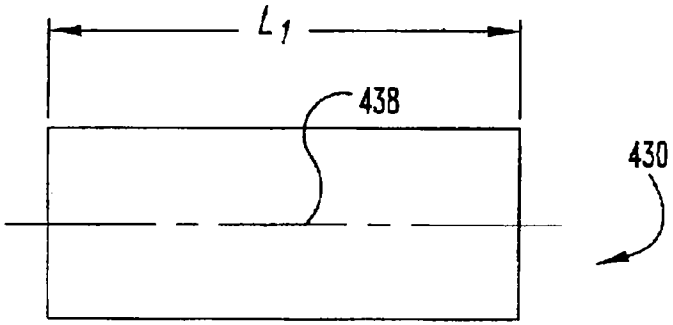
FIG. 42 is an elevational view of a stop member comprising a portion of the rod reducer instrument of FIG. 25.
Figure 43:
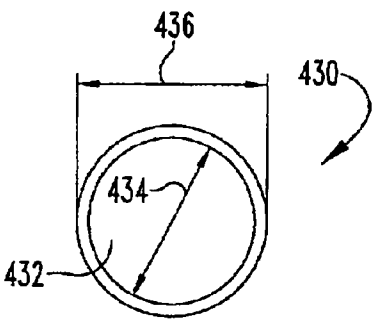
FIG. 43 is an end elevational view of the stop member of FIG. 42.

As reducing member 400 is moved distally, its distal end 408 contacts rod R and moves it distally towards fastener F. The surgeon can then insert the set screw or cap through passage 382 of fastener engaging member 380 to secure rod R in yoke Y. Passage 382 can be sized and configured to closely fit with the driver used to install the set screw to ensure proper alignment between the set screw and the yoke. To prevent reducing member 400 from being extended too far proximally, proximal end 387 of fastener engaging member 380 has a stop member 430, shown also in FIGS. 42-43, secured thereto. Stop member 430 has an inner diameter that fits over fastener engaging member 380 and is welded or otherwise fastened to its proximal end 387. Stop member 430 has a hollow passage 432 extending along longitudinal axis 436 that forms an extension of passage 382 of fastener engaging member 380. Stop member 430 has an outer diameter 436 that extends about fastener engaging member 380 and interferes with a driving member 440 secured to proximal end 406 of reducing member 400 to limit proximal movement of reducing member 400. Stop member 430 further has a length L1 that allows stop member 430 to extend proximally a sufficient distance from fastener engaging member 380 to interfere with closed arms 352, 354 of actuator assembly 350 to limit distal movement of reducing member 400.

Figure 35:
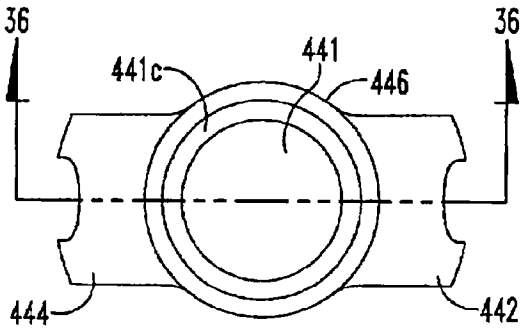
FIG. 35 is a plan view of a driving member comprising a portion of the rod reducer instrument of FIG. 25.
Figure 36:
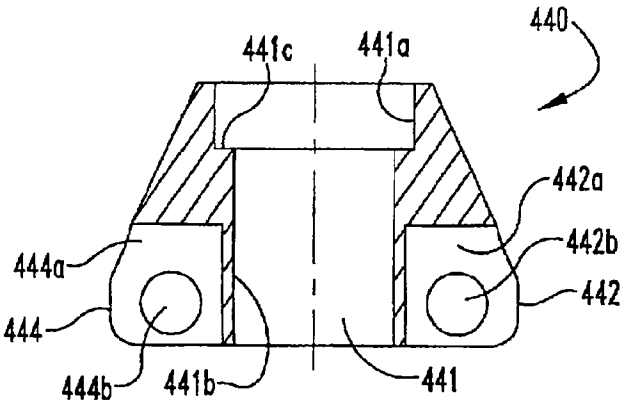
FIG. 36 is a cross-sectional view taken through line 36-36 of FIG. 35.
Figure 37:
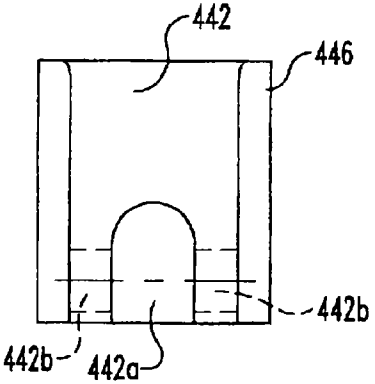
FIG. 37 is a side elevational view of the driving member of FIG. 35.
Figure 41:
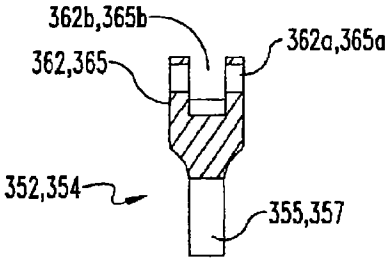
FIG. 41 is a cross-sectional view through line 41-41 of FIG. 38.
Figure 38:
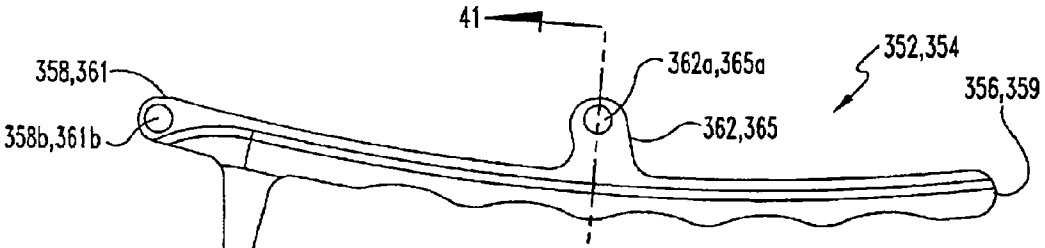
FIG. 38 is an elevational view of a handle comprising a portion of the rod reducer instrument of FIG. 25.
Figure 39:
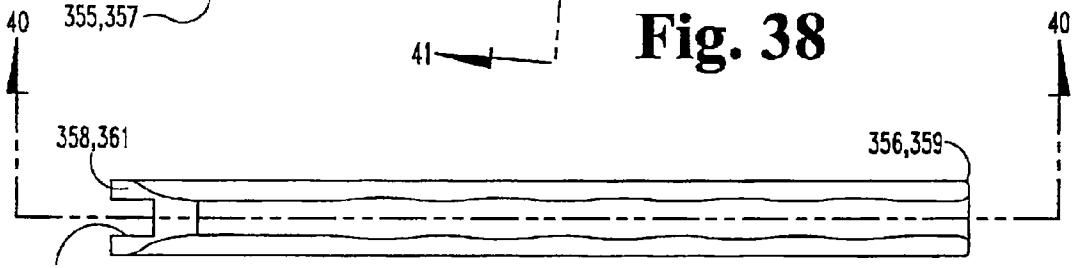
FIG. 39 is an elevational view of the handle of FIG. 38 rotated ninety degrees about its longitudinal axis from its orientation in FIG. 38.
Figure 40:
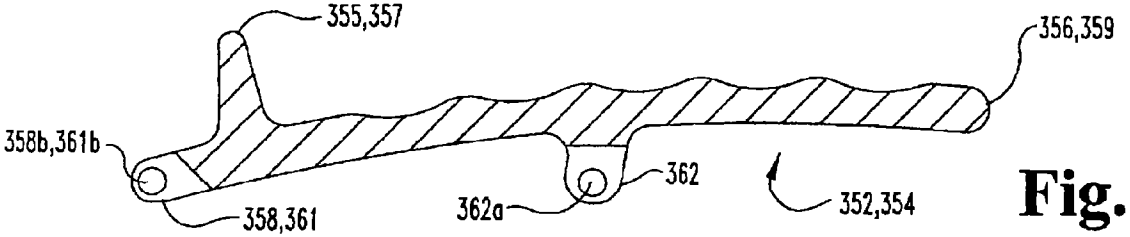
FIG. 40 is a cross-sectional view through line 40-40 of FIG. 39.

As shown in FIGS. 35-37, driving member 440 has a body 446 defining a passage 441 therethrough. Passage 441 has a first larger portion 441a sized to fit over proximal end 406 of reducing member 400 where it is welded or otherwise attached thereto. Passage 444 is stepped down to a smaller diameter portion 441b in order to provide a rim 441c which can be seated on proximal end 406 of reducing member 400. Smaller portion 441b is sized to slidingly receive fastener engaging member 380 therethrough yet allow body 446 to contact stop member 430 to limit proximal movement of reducing member 400 as discussed above.

Figure 44:
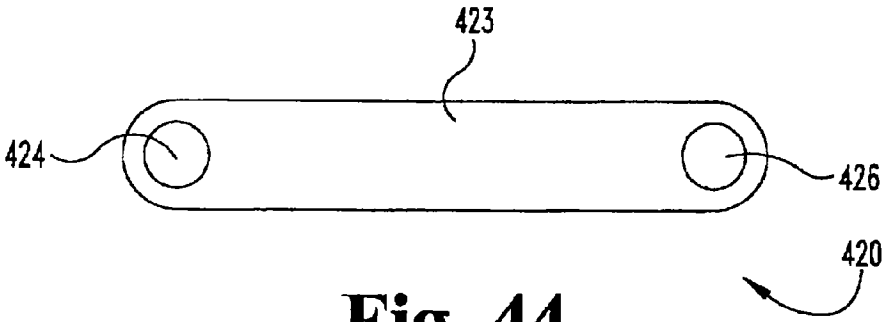
FIG. 44 is an elevational view of a link comprising a portion of the rod reducer instrument of FIG. 25.

As shown in FIG. 44, first link 420 includes a body 423 having first hole 424 at a distal end thereof and a second hole 426 at an opposite proximal end thereof. Second link 422 is identical to first link 420, and each comprise a portion of actuator assembly 351. Referring back to FIGS. 35-37, driving member 440 further includes a first ear 442 having a female receptacle 442a into which one end of first link 420 can be placed. A pin 363 can be placed through holes 442b and first hole 424 of first link 420 to pivotally couple the distal end of link 420 thereto. Similarly, second ear 444 can be provided with a female receptacle 444a into which one end of second link 422 can be placed. Second ear 444 includes holes 444b in communication with female receptacle 444a. A pin 366 can be placed through holes 444b to pivotally couple the distal end of second link 422 therewith.

Referring now to FIGS. 38-41, first arm 352 and second arm 354 of actuator assembly 351 will be described. First arm 352 and second arm 354 are identical. Each arm 352, 354 extends between a proximal end 356, 359 and distal end 358, 361 respectively. Each arm 352, 354 can include an arcuate profile therealong with gripping portions to accommodate the hands and fingers of a surgeon's grip. Distal end 358, 361 includes female receptacle 358a, 361a having holes 358b, 361b in communication therewith. Female receptacle 358a, 361a is sized to receive respective ones of the ears 396, 398 of fastener engaging member 380 therein. Pins 437, 439 extend through respective ones of the holes 358a, 361a and ears 396, 398 to pivotally couple distal end 358, 361 of arms 352, 354 thereto.

Each of the arms 352, 354 has a medially extending female connector 362, 365 defining a hole 362a, 365a therethrough and a receptacle 362b, 365b in communication with hole 362a, 365a. Receptacles 362b, 365b are each sized to receive the proximal end of a respective one of the first and second links 420, 422. Pins 367, 369 extend through through-holes 362a, 365a to pivotally couple first arm 352 and second arm 354 to first link 420 and second link 422, respectively. While not required, rod reducer instrument 350 can include a locking mechanism (not shown) which holds actuator assembly 351 in its reduced position shown in FIG. 27.

It is further contemplated that the rod reducer instruments of the present invention can be inserted through an access tube used in minimally invasive procedures to install fasteners F and perform other procedure on the spine. In FIG. 26, an access tube 450 is shown in section view and positioned through skin S over fastener F and rod R. Such access tubes are used in thorascopic, laparoscopic, and other minimally invasive approaches to the spine. Since it is contemplated that the fastener engaging member and reducing member of the rod reducer instruments of the present invention can be provided such that they move along the same central axis, the space needed to reduce rod R is minimized. Thus rod reduction can be accomplished with a minimally invasive approach to minimize tissue resection, cutting and the like to access the surgical site.

Rod reducer instrument 350 includes a laterally extending member 355, 357 extending from each of the arms 352, 354 to contact the proximal end of access tube 450 to limit the insertion depth of rod reducer instrument 350 therein. It should be understood that such laterally extending members could be provided with the other rod reducer instruments described herein, and located on other components thereof such as on fastener engaging members 80, 380.

A method for using rod reducer instrument 350 will now be described. The surgeon has positioned fastener F into vertebra V1 and placed rod R in close proximity to yoke Y of fastener F. Rod reducer instrument 350 is in its normally biased open position of FIG. 25 in which arms 352, 354 are spaced apart from one another. Rod reducer instrument 350 is introduced through an open incision or an access port to fastener F. Fastener engaging member 380 is placed around rod R so that rod R is in the channels formed by slots 391, 393. Distal end 388 can be placed over yoke Y since flex arms 390, 392 move outwardly to pass over yoke Y until protrusions 394, 396 engage indentations in yoke Y. Arms 352, 354 are moved towards one another to move reducing member 400 distally along fastener engaging member 380 to push or reduce rod R into yoke Y a sufficient distance to allow attachment of a set screw or cap to yoke Y. This distal movement of reducing member 400 is effected by the first and second links 420, 422 pivoting at their ends coupled to arms 352, 354 and also pivoting at their ends coupled to driving member 440, which thereby drives reducing member 400 distally and into contact with rod R. Actuator assembly 351 can be held in the position of FIG. 27 to maintain rod R in its reduced position as the surgeon installs the set screw in yoke Y through passage 382 of fastener engaging member 380. Once the set screw is firmly seated against rod R, arms 352, 354 are released and returned to their open position of FIG. 25. Flex arms 390 and 392 allow release of protrusions 394, 396 from yoke Y. Rod reducer instrument 350 can then be removed and repeated as needed to reduce rod R into other fasteners.

The rod reducer instruments of the present invention are preferably made of a sturdy biocompatible material such as stainless steel using standard fabrication techniques for medical grade instruments. However, other biocompatible materials are also contemplated.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical instrument for reducing a rod toward a bone fastener, comprising:

a fastener engaging member extending between a proximal end and a distal end, a distal portion of said fastener engaging member adapted to engage the bone fastener;

a reducing member positioned along and movable relative to said fastener engaging member, said reducing member having a distal end *and a longitudinal axis oriented in its direction of movement*; and an actuator assembly pivotally coupled to said fastener engaging member and pivotally coupled to said reducing member, *said actuator comprising a first arm and a second arm,* wherein said actuator assembly is operable to move said reducing member distally with respect to said fastener engaging member *when proximal ends of said first and second arms are biased together,* whereby, *with biasing together of said first and second arms,* said distal end of said reducing member contacts the rod to move the rod *distally, relative to the fastener engaging member,* toward the bone fastener,

*wherein a plane along which said first and second arms move is offset from the longitudinal axis.*

2. The instrument of claim 1, wherein said reducing member is positioned about said fastener engaging member.

3. The instrument of claim 1, wherein said actuator assembly is adapted to receive a portion of the rod therein.

4. The instrument of claim 1, wherein [said actuator assembly includes a lateral offset to position] a proximal portion of said actuator assembly *is offset* away from a proximal end opening of a passage extending through said fastener engaging member.

5. The instrument of claim 1, wherein said [actuator assembly includes a] first arm *is* pivotally coupled to [a] *said* second arm.

6. The instrument of claim 5, wherein:

said first arm includes a joint between a proximal end and a distal end of said first arm, said joint defining a proximal portion and a distal portion of said first arm;

said second arm includes a joint between a proximal end and a distal end of said second arm, said joint defining a proximal portion and a distal portion of said second arm; and said proximal portion of said first arm and said proximal portion of said second arm are each pivotal about a respective one of said joints to orient said proximal portions transversely to said distal portions.

7. The instrument of claim 1, wherein said actuator assembly includes a locking mechanism to hold said reducing member in a reduced position.

8. The instrument of claim 1, wherein said actuator assembly is spring biased to a reducing member retracted position.

9. The instrument of claim 1, wherein said fastener engaging member includes a pair of flex arms extending proximally from said distal end thereof.

10. The instrument of claim 9, wherein said fastener engaging member includes a prong at the distal end of each of said flex arms, each of said prongs defining a channel for receiving the rod therein.

11. The instrument of claim 10, wherein said reducing member is positionable over at least a portion of said prongs.

12. The instrument of claim 9, wherein said fastener engaging member includes a pair of elongated slots extending between said flex arms opening at said distal end.

13. The instrument of claim 12, wherein said reducing member includes at least one slot through a sidewall thereof in communication with one of said elongated slots of said fastener engaging member.

14. The instrument of claim 1, wherein said fastener engaging member and said reducing member are reciprocally slidably coupled.

15. The instrument of claim 1, wherein said reducing member and said fastener engaging member each include a generally circular cross-section.

16. The instrument of claim 1, wherein:

said fastener engaging member has a longitudinal axis extending proximally and distally therethrough; and said reducing member has a longitudinal axis extending proximally and distally therethrough, said longitudinal axis of said reducing member being generally positioned along said longitudinal axis of said fastener engaging member.

17. The instrument of claim 1, wherein said actuator assembly includes:

a first link having a distal end pivotally coupled to a first side of said reducing member;

a first pivot arm having a distal end pivotally coupled to a proximal end of said first link, said first pivot arm having a medially extending connector pivotally coupled to said fastener engaging member;

a first arm having a distal end pivotally coupled to a proximal end of said first pivot arm, said first arm having a proximal portion extending proximally from a medially extending connector;

a second link having a distal end pivotally coupled to a second side of said reducing member opposite said first side;

a second pivot arm having a distal end pivotally coupled to a proximal end of said second link, said second pivot arm having a medially extending connector pivotally coupled to said medially extending connector of said first pivot arm and also pivotally coupled to said fastener engaging member; and a second arm having a medially extending connector pivotally coupled to said medially extending connector of said first arm, said second arm having a distal end pivotally coupled to a proximal end of said second pivot arm, said second arm further having a proximal portion extending proximally of said medially extending connector of said second arm.

18. The instrument of claim 1, wherein said actuator assembly includes:

a first link having a distal end pivotally coupled to said reducing member;

a first arm having a distal end pivotally coupled to said fastener engaging member, said first arm extending to a proximal end, said first arm further being pivotally coupled between said proximal and distal ends to a proximal end of said first link;

a second link having a distal end pivotally coupled to said reducing member opposite said first link; and a second arm having a distal end pivotally coupled to said fastener engaging member opposite said first arm, said second arm extending to a proximal end and being pivotally coupled between said proximal and distal ends to a proximal end of said second link.

19. The instrument of claim 18, further comprising a stop member at said proximal end of said fastener engaging member to limit proximal movement of said reducing member.

20. A surgical instrument for reducing a rod toward a bone fastener, comprising:

a fastener engaging member having a passage extending between a proximal end and a distal end, a distal portion of said fastener engaging member being adapted to engage the bone fastener, *the passage having a longitudinal axis*;

a reducing member movably disposed with respect to said fastener engaging member, said reducing member having a distal end;

an actuator assembly coupled between said fastener engaging member and said reducing member [and], *said actuator* including a proximal portion, extending proximally of said reducing member and said fastener engaging member, *a first arm and a second arm, wherein* (*i*) at least a portion of said actuator assembly [being] *is* offset laterally with respect to said fastener engaging member to locate said proximal portion of said actuator assembly away from a proximal end opening of said passage of said fastener engaging member, [wherein] (*ii*) said actuator assembly is operable to move said reducing member *distally, relative to said fastener engaging member,* to contact the rod to move the rod and bone fastener toward one another, (*iii*) *proximal ends of said first and second arms are biased together to move the rod distally toward the bone fastener, and* (*iv*) *a plane along which said first and second arms move is offset from the longitudinal axis*.

21. The instrument of claim 20, wherein said actuator assembly is operable to move said reducing member distally with respect to said fastener engaging member.

22. The instrument of claim 20, wherein [said actuator assembly includes a lateral offset portion to laterally offset] said proximal portion of said actuator assembly *is offset* away from a proximal end opening of said passage of said fastener engaging member.

23. The instrument of claim 20, wherein said reducing member is positioned about said fastener engaging member and slidable with respect thereto in response to operation of said actuator assembly.

24. The instrument of claim 23, wherein said distal end of said fastener engaging member includes a pair of prongs forming a rod passage.

25. The instrument of claim 24, wherein said reducing member and said distal end of said fastener engaging member are configured such that said reducing member exerts inward pressure on at least one of said prongs when said reducing member is positioned over said prongs.

26. The instrument of claim 20, wherein:

said fastener engaging member has a longitudinal axis extending proximally and distally therethrough; and said reducing member has a longitudinal axis extending proximally and distally therethrough, said longitudinal axis of said reducing member being generally positioned along said longitudinal axis of said fastener engaging member.

27. The instrument of claim 20, wherein said [actuator assembly includes a] first arm *is* pivotally coupled to [a] *said* second arm.

28. The instrument of claim 27, wherein:

said first arm includes a joint between a proximal end and a distal end of said first arm, said joint defining a proximal portion and a distal portion of said first arm;

said second arm includes a joint between a proximal end and a distal end of said second arm, said joint defining a proximal portion and a distal portion of said second arm; and said proximal portion of said first arm and said proximal portion of said second arm are each pivotal about a respective one of said joints to orient said proximal portions transversely to said distal portions.

29. The instrument of claim 27 wherein said first arm and said second arm are spring biased away from one another.

30. The instrument of claim 20, wherein said actuator assembly includes a locking mechanism to hold said reducing member in a reduced position.

31. The instrument of claim 20, wherein said fastener engaging member includes a pair of flex arms extending proximally from said distal end thereof.

32. The instrument of claim 20, wherein each of said flex arms includes a prong at a distal end thereof, each of said prongs defining a channel for receiving the rod therein.

33. The instrument of claim 32, wherein said fastener engaging member includes a pair of elongated slots extending between said flex arms to said distal end.

34. A method of positioning an elongated implant member in a patient, comprising:

fixing a fastener to a patient;

placing an elongated implant member adjacent said fastener;

providing a rod reducer instrument;

inserting said rod reducer instrument through an access tube providing access to said fastener and said elongated implant member;

engaging a distal portion of a fastener engaging member of said rod reducer instrument to said fastener; and moving a reducing member of said rod reducer instrument distally so that said reducing member contacts said elongated implant member and moves said elongated implant member toward said fastener, *said moving step comprising biasing together proximal ends of first and second arms of an actuator to move said reducing member distally to move said elongated implant member toward said fastener,*

*wherein the reducing member has a longitudinal axis oriented in a reducing direction and the first and second arms move along a plane offset from the longitudinal axis to move said reducing member*.

35. The method of claim 34; further comprising:

positioning said elongated implant member adjacent said fastener with said reducing member; and engaging said elongated implant member to said fastener through said access tube.

36. The method of claim 34, further comprising moving said reducing member about said fastener engaging member to contact said elongated implant member.

37. The method of claim 34, further comprising:

fixing a second fastener to a patient;

modifying said reducing member of said rod reducer instrument;

engaging the distal portion of the fastener engaging member of the modified rod reducer instrument to said second fastener; and moving said modified reducing member distally with respect to said fastener engaging member so that said modified rod reducer member contacts said elongated implant member and moves said elongated implant member toward said second fastener.

38. The method of claim 34, further comprising placing said fastener engaging member about said elongated implant member.

39. The method of claim 34, further comprising:

positioning said elongated implant member adjacent said fastener with said reducing member;

placing a fastener through a passage defined by said fastener engaging member; and securing said elongated implant member to said fastener through said access tube.

40. A method of securing an elongated implant member to a fastener, comprising:

coupling a rod reducer instrument to the fastener, said rod reducer instrument having a passage extending therethrough, *along a longitudinal axis,* in communication with said fastener;

moving a reducing member of said rod reducer instrument distally so that said reducing member contacts said elongated implant member and positions said elongated implant member adjacent said fastener, *said moving step comprising biasing proximal ends of first and second arms of an actuator together to move said reducing member distally to position said elongated implant member adjacent said fastener;* and securing said elongated implant member to said fastener through said passage,

*wherein the first and second arms move along a plane offset from the longitudinal axis to move said reducing member.*

41. The method of claim 40, wherein said rod reducer instrument includes a fastener engaging member engagable to said fastener and defining said passage therethrough.

42. The method of claim 41, wherein said reducing member is positioned about said fastener engaging member.

43. The method of claim 40, further comprising inserting the rod reducer instrument through an access tube to the fastener.

*44. The instrument of claim 1, wherein said surgical instrument includes a viewing area for visualization of the rod and bone fastener when said reducing member brings the rod into contact with the bone fastener.*

*45. The instrument of claim 20, wherein said surgical instrument includes a viewing area for visualization of the rod and bone fastener when said reducing member brings the rod into contact with the bone fastener.*

*46. The method of claim 34, further comprising viewing said elongated implant member and fastener during said moving step when said elongated implant member and fastener are brought into contact.*

*47. The method of claim 40, further comprising viewing said elongated implant member and said fastener during said moving step when said elongated implant member and fastener are moved adjacent each other.*

*48. The instrument of claim 1, wherein said first and second arms are actuated about a common pivot axis located between proximal and distal ends of said first and second arms.*

*49. The instrument of claim 1, wherein the longitudinal axis intersects a pivot axis about which said first and second arms pivot.*

*50. The instrument of claim 2, wherein the longitudinal axis intersects a pivot axis about which said first and second arms pivot.*

*51. The instrument of claim 1, wherein said fastener engaging member defines a passage, along the longitudinal axis, having first and second openings aligned with the longitudinal axis, with said first opening of said passage being at said distal portion of said fastener engaging member, and*

*wherein said first and second arms are pivotally coupled to each other at a position along said instrument spaced proximally from said second opening.*

*52. The instrument of claim 1, wherein said first arm is pivotally coupled to said second arm,*

*said fastener engaging member and said reducing member are reciprocally slidably coupled,*

*said first and second arms are actuated about a common pivot axis located between proximal and distal ends of said first and second arms, and*

*said reducing member moves the rod in a longitudinally oriented direction with respect to the bone fastener.*

*53. The instrument of claim 52, wherein said fastener engaging member includes a pair of flex arms extending proximally from said distal end thereof, and said reducing member and said fastener engaging member each include a generally circular cross-section.*

*54. The instrument of claim 20, wherein the longitudinal axis intersects a pivot axis about which said first and second arms pivot.*

*55. The instrument of claim 20, wherein said passage extends along the longitudinal axis between said proximal end opening and a distal end opening, said openings being aligned with the longitudinal axis, and*

*wherein said first and second arms are pivotally coupled to each other at a position along said instrument spaced proximally from said proximal end opening.*

*56. The method of claim 40, wherein an engaging member for performing the coupling in said coupling step includes a pair of elongated slots extending between a pair of flex arms, which open at a distal end thereof.*

*57. The method of claim 40, wherein said sub-step moves said elongated implant member in a longitudinal direction with respect to said rod reducer instrument.*

*58. The method of claim 40, wherein said sub-step moves said elongated member in a longitudinally oriented direction with respect to said fastener.*

*59. The method of claim 58, wherein said first and second arms are actuated about a common pivot axis located between proximal and distal ends of said first and second arms.*

*60. The instrument of claim 40, wherein the longitudinal axis of said reducing member intersects a pivot axis about which said first and second arms pivot.*

*61. The method of claim 40, wherein said passage has first and second openings aligned with the longitudinal axis, with said first opening of said passage being at a distal portion of said rod reducer instrument, and*

*wherein said first and second arms are pivotally coupled to each other at a position along said rod reducer instrument spaced proximally from said second opening.*

*62. The instrument of claim 1, wherein the plane and the longitudinal axis are offset by less than 30 mm.*

*63. The instrument of claim 1, wherein the plane and the longitudinal axis do not intersect.*

*64. A surgical instrument for reducing a rod toward a bone fastener, comprising:*

*a fastener engaging member extending between a proximal end and a distal end, a distal portion of said fastener engaging member adapted to engage the bone fastener;*

*a reducing member positioned along and movable relative to said fastener engaging member, said reducing member having a distal end and a longitudinal axis oriented in the direction of movement; and*

*an actuator assembly pivotally coupled to said fastener engaging member and pivotally coupled to said reducing member, said actuator comprising a first arm and a second arm, wherein said actuator assembly is operable to move said reducing member distally with respect to said fastener engaging member when proximal free ends of said first and second arms are biased together, whereby said distal end of said reducing member contacts the rod to move the rod toward the bone fastener,*

*wherein said first and second arm further comprise respective distal ends and are interconnected at intermediate positions such that said distal ends move apart when the proximal free ends are biased together,*

*wherein said first and second handles extend laterally away from the longitudinal axis, and*

*wherein said fastener engaging member and said reducing member define an open passage to the rod, along the longitudinal axis, during actuation by said actuator assembly.*

*65. A surgical instrument for reducing a rod toward a bone fastener, comprising:*

*a fastener engaging member extending between a proximal end and a distal end, a distal portion of said fastener engaging member adapted to engage the bone fastener;*

*a reducing member positioned along and movable relative to said fastener engaging member, said reducing member having a distal end and a longitudinal axis oriented in its direction of movement; and*

*an actuator assembly pivotally coupled to said fastener engaging member and pivotally coupled to said reducing member, said actuator comprising a first arm and a second arm, wherein said actuator assembly is operable to move said reducing member distally with respect to said fastener engaging member when proximal ends of said first and second arms are biased together, whereby, with biasing together of said first and second arms, said distal end of said reducing member contacts the rod to move the rod distally, relative to the fastener engaging member, toward the bone fastener,*

*wherein said first and second arms are connected at an intermediate connection point such that the biasing together of proximal ends of said first and second arms moves apart the distal ends of said first and second arms.*

*66. The surgical instrument of claim 65, wherein said proximal ends of said first and second arms and said connection point of said actuator assembly are offset laterally from an extending direction of said fastener engaging member, to position said proximal ends of said first and second arms and said connection point away from a proximal end opening of a passage extending through said fastener engaging member.*

*67. The surgical instrument of claim 65, wherein the distal end of said fastener engaging member defines opposing arms that engage the bone fastener.*

*68. The surgical instrument of claim 67, wherein a side gap defined by said opposing arms of said fastener engaging member aligns with a side gap of the bone fastener that receives the rod.*

*69. The surgical instrument of claim 66, further comprising a biasing mechanism for biasing apart the proximal ends of said first and second arms.*

*70. The surgical instrument of claim 69, further comprising a locking system that secures said proximal ends of said first and second arms relative to each other to prevent said proximal ends from spreading apart in response to said biasing mechanism.*

*71. The surgical instrument of claim 70, wherein said locking system can secure said proximal ends of said first and second arms relative to each other at a plurality of positions, each position providing a different distance between said proximal ends of said first and second arms.*

*72. The surgical instrument of claim 69, wherein said biasing mechanism includes a leaf spring.*

*73. The surgical instrument of claim 65, wherein the distal end of at least one of said first and second arms includes a hole, and*

*wherein said at least one of first and second arms pivots about said hole when a pin is provided in said hole.*

*74. The surgical instrument of claim 65, wherein said reducing member engages a surface of said fastener engaging member to limit an amount of play of said reducing member.*

*75. The surgical instrument of claim 65, wherein said reducing member includes a lip adapted to limit a longitudinal movement of said reducing member relative to said fastener engaging member.*

*76. The surgical instrument of claim 65, wherein said fastener engaging member includes a rim adapted to limit a longitudinal movement of said reducing member relative to said fastener engaging member.*

*77. The surgical instrument of claim 65, wherein said reducing member includes a substantially cylindrical body.*

*78. The surgical instrument of claim 65, wherein said reducing member includes a body having a circular cross-section.*

*79. The surgical instrument of claim 65, further comprising a third arm pivotally coupled to the distal end of one of said first and second arms,*

*wherein the biasing together of said first and second arms pivots the distal end of the one of said first and second arms with respect to said third arm, to move the reducing member distally with respect to said fastener engaging member.*

*80. The surgical instrument of claim 66, further comprising a third arm, wherein a first portion of said third arm is pivotally coupled to the distal end of one of said first and second arms, and the biasing together of said first and second arms pivots the distal end of the one of said first and second arms with respect to said third arm, to move the reducing member distally with respect to said fastener engaging member.*

* * * * *